United States Patent [19]

Prücher et al.

[11] 4,285,961
[45] Aug. 25, 1981

[54] BASIC THIOETHERS

[75] Inventors: Helmut Prücher, Heppenheim; Jürgen Uhl, Seeheim; Hans-Adolf Kurmeier, Darmstadt; Volkmar Rudolph, Seeheim; Helmut Wahlig, Darmstadt, all of Fed. Rep. of Germany

[73] Assignee: Merck Patent Gesellschaft mit beschrankter Haftung, Darmstadt, Fed. Rep. of Germany

[21] Appl. No.: 82,456

[22] Filed: Oct. 9, 1979

Related U.S. Application Data

[63] Continuation of Ser. No. 926,350, Jul. 20, 1978, abandoned.

[30] Foreign Application Priority Data

Jul. 20, 1977 [DE] Fed. Rep. of Germany ....... 2732750

[51] Int. Cl.³ .................. A61K 31/415; C07D 233/20
[52] U.S. Cl. ......................... 424/273 R; 260/465.5 R; 424/269; 424/275; 425/325; 425/330; 542/469; 542/470; 542/474; 548/265; 548/337
[58] Field of Search .......... 260/570.6, 570.9, 570.8 R, 260/329.3, 570 R; 548/337; 549/49; 542/469, 470, 474, 269; 424/273 R

[56] References Cited

U.S. PATENT DOCUMENTS

| | | | |
|---|---|---|---|
| 2,742,500 | 4/1956 | Gregory et al. | 260/570.6 |
| 3,557,148 | 1/1971 | Moed et al. | 260/570.6 |
| 3,954,871 | 5/1976 | Buu-Hoi et al. | 260/570.6 |
| 4,006,243 | 2/1977 | Strehlke et al. | 548/335 |
| 4,123,555 | 10/1978 | Mehta et al. | 260/570.8 R |

OTHER PUBLICATIONS

Fujiwara et al., J. Heterocyclic Chemistry, vol. 6, pp. 379-387 (1969).
Blank et al., J. Med. Chem., vol. 12, pp. 271 to 276 (1969).
Sterescu et al., Chem. Abst., vol. 58, col. 240 (1963), (abst. of Rev. Chim., vol. 11, pp. 487-488 (1960).

*Primary Examiner*—John D. Randolph
*Attorney, Agent, or Firm*—Millen & White

[57] ABSTRACT

Basic thioethers of the formula

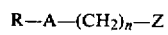

$$R-A-(CH_2)_n-Z$$

wherein R is p-$R^5$-S-phenyl or 2-dibenzothienyl; A is —$CHR^3$—$CHR^4$—, —$CR^3(OH)$—$CHR^4$—, —$CHR^3$—$CR^4(OH)$— or —$CR^3$=$CR^4$—; Z is —$NR^1R^2$, 1-imidazolyl or 1,2,4-triazol-1-yl; n is 1, 2 or 3; $R^1$ and $R^2$ are the same or different and each is H, alkyl of 1-4 carbon atoms or together form alkylene of 4-7 ring carbon atoms, or form 3-oxapentamethylene; $R^3$ and $R^4$ are the same or different and each is H, alkyl of 1-4 carbon atoms or phenyl; $R^5$ is an unsubstituted phenyl or benzyl group or a phenyl or benzyl group substituted with 1 or 2 of halogen, nitro, amino and/or alkoxy of 1-4 carbon atoms, alkyl of 1-6 carbon atoms, or cycloalkyl of 3-7 ring carbon atoms, with the proviso that $R^5$ is alkyl of 1-6 carbon atoms, or cycloalkyl of 3-7 ring carbon atoms when A is —$CHR^3$—$CH_2$— and Z is 1-imidazolyl possess valuable pharmacological properties.

7 Claims, No Drawings

BASIC THIOETHERS

This is a continuation, or application Ser. No. 926,350 filed July 20, 1978 now abandoned.

BACKGROUND OF THE INVENTION

The invention concerns new basic thioethers having pharmacological properties. Other thioethers are known from U.S. Pat. No. 4,006,243.

SUMMARY OF THE INVENTION

It is an object of this invention to provide new compounds which can be employed for the preparation of medicaments.

Upon further study of the specification and appended claims, further objects and advantages of this invention will become apparent to those skilled in the art.

These objects have been attained by providing the basic thioethers of formula I

$$R-A-(CH_2)_n-Z \quad (I)$$

wherein R is p-$R^5$-S-phenyl or 2-dibenzothienyl; A is —$CHR^3$—$CHR^4$—, —$CR^3(OH)$—$CHR^4$—, —$CHR^3$—$CR^4(OH)$— or —$CR^3$=$CR^4$—; Z is —$NR^1R^2$, 1-imidazolyl or 1,2,4-triazol-1-yl; n is 1, 2 or 3; $R^1$ and $R^2$ are the same or different and each is H or alkyl of 1–4 carbon atoms or together form alkylene of 4–7 ring carbon atoms optionally substituted by $C_{1-2}$ alkyl wherein the total number of carbon atoms in the $R_1$-$R_2$-group is 7 or less; or form 3-oxapentamethylene; $R^3$ and $R^4$ are the same or different and each is H, alkyl of 1–4 carbon atoms or phenyl; $R^5$ is an unsubstituted phenyl or benzyl group or a phenyl or benzyl group substituted with 1 or 2 of halogen, nitro, amino and/or alkoxy of 1–4 carbon atoms, alkyl of 1–6 carbon atoms or cycloalkyl of 3–7 ring carbon atoms with the proviso that $R^5$ is an alkyl group of 1–6 carbon atoms or a cycloalkyl group of 3–7 ring carbon atoms when A is —$CHR^3$—$CH_2$— and Z is 1-imidazolyl; and their physiologically acceptable acid-addition salts.

DETAILED DISCUSSION

For all of the above-mentioned radicals, alkyl preferably is methyl or ethyl, and also is n-propyl, isopropyl, n-butyl, isobutyl, sec-butyl or tert-butyl. Furthermore, for $R^5$, suitable alkyls include, for example, 1-, 2- or 3-pentyl, 2-methyl-1-butyl, isopentyl, 3-methyl-1-butyl, 3-methyl-2-butyl, tert-pentyl, neopentyl, 1-, 2- or 3-hexyl, 2-methyl-1-, -2- or -3-pentyl, isohexyl, 4-methyl-1-pentyl, 4-methyl-2-pentyl, 3-methyl-1-, -2- or -3-pentyl, 2-ethyl-1-butyl, 2,3-dimethyl-1- or -2-butyl, 2,2-dimethyl-1-butyl, 3,3-dimethyl-1- or -2-butyl.

Suitable alkylene groups for $R_1$ and $R_2$ are straight-chained or branched and include e.g., tetramethylene, 1- or 2-methyl-tetramethylene, pentamethylene, 1-, 2- or 3-methylpentamethylene, 1-, 2- or 3-ethylpentamethylene, 1,1-, 1,2-, 1,3-, 1,4-, 1,5-, 2,2-, 2,3-, 2,4- or 3,3-dimethylpentamethylene, hexamethylene, heptamethylene, etc. The total number of carbon atoms in the $R_1$-$R_2$-alkylene groups is 7 or less.

Suitable alkoxy groups (for substituted $R^5$) include, for example, preferably methoxy or ethoxy, and also n-propyloxy, isopropyloxy, n-butyloxy, isobutyloxy, sec-butyloxy or tert-butyloxy.

Suitable cycloalkyl groups include, for example, cyclopropyl, cyclobutyl, cyclopentyl, cyclohexyl, or cycloheptyl, furthermore, e.g., 1-, 2-, or 3-methylcyclopentyl, 1-, 2-, 3- or 4-methyl-cyclohexyl, etc.

Suitable halogen preferably is chlorine or bromine, but fluorine and iodine are also included.

In particular, $R^1$ and $R^2$ preferably are H, methyl or ethyl. $R^3$ and $R^4$ preferably are H, methyl or phenyl. $R^5$ is preferably an unsubstituted phenyl or benzyl group or a phenyl or benzyl group substituted 1 or 2 times by halogen, especially chlorine, in particular, e.g., phenyl, o-, m- or p-fluorophenyl, o-, m- or p-chlorophenyl, o-, m- or p-bromophenyl, o-, m- or p-iodophenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, dibromophenyl, such as 2,4-dibromophenyl, diiodophenyl, such as 2,4-diiodophenyl, chlorofluorophenyl, such as 2-fluoro-4-chlorophenyl or 2-chloro-4-fluorophenyl, o-, m- or p-nitrophenyl, dinitrophenyl, such as 2,4- or 3,5-dinitrophenyl, o-, m- or p-aminophenyl, diaminophenyl, such as 2,4- or 3,5-diaminophenyl, o-, m- or p-methoxyphenyl, o-, m- or p-ethoxyphenyl, o-, m- or p-isobutoxyphenyl, 2,3-, 2,4-, 2,5-, 2,6-, 3,4- or 3,5-dimethoxyphenyl, benzyl, o-, m- or p-fluorobenzyl, o-, m- or p-chlorobenzyl, o-, m- or p-bromobenzyl, o-, m- or p-iodobenzyl, 2,3-, 2,4-, 2,5-, 2,6-, 3,4- or 3,5-difluorobenzyl, 2,3-, 2,4-, 2,5-, 2,6-, 3,4- or 3,5-dichlorobenzyl, 2,3-, 2,4-, 2,5-, 2,6-, 3,4- or 3,5-dibromobenzyl, diiodobenzyl, such as 2,4-diiodobenzyl, chlorofluorobenzyl, such as 2-fluoro-4-chlorobenzyl or 2-chloro-4-fluorobenzyl, bromochlorobenzyl, such as 2-bromo-4-chlorobenzyl or 2-chloro-4-bromobenzyl, o-, m- or p-nitrobenzyl, dinitrobenzyl, such as 2,4- or 3,5-dinitrobenzyl, o-, m- or p-aminobenzyl, diaminobenzyl, such as 2,4- or 3,5-diaminobenzyl, o-, m- or p-methoxybenzyl, o-, m- or p-ethoxybenzyl, o-, m- or p-isobutoxybenzyl or 2,3-, 2,4-, 2,5-, 2,6-, 3,4- or 3,5-dimethoxybenzyl. Furthermore, $R^5$ is preferably methyl, ethyl, branched alkyl, such as isopropyl, isobutyl, (especially) isopentyl or isohexyl, or cyclohexyl when A is $CHR^3CH_2$ and Z is 1-imidazolyl. In general, the substitution on the phenyl or benzyl group is preferably in the p position(s).

Consequently, R preferably is p-phenylthiophenyl, p-(p-chlorophenylthio)-phenyl, p-benzylthiophenyl, p-(2,4-dichlorobenzylthio)-phenyl, p-isopentylthiophenyl, p-cyclohexylthiophenyl or 2-dibenzothienyl.

A preferably is —$CR^3$=$CR^4$—, in particular especially the following: —$CH_2$—$CH_2$—, —$CH_2$—$CH(CH_3)$—, —$CH(CH_3)$—$CH_2$—, —$CH(CH_3)$—$CH(CH_3)$—, —$CH(C_6H_5)$—$CH_2$—, —$CH(C_6H_5)$—$CH(CH_3)$—, —$CHOH$—$CH_2$, —$CHOH$—$CH(CH_3)$—, —$C(CH_3)(OH)$—$CH_2$—, —$C(CH_3)(OH)$—$CH(CH_3)$—, —$C(C_6H_5)(OH)$—$CH_2$—, —$C(C_6H_5)(OH)$—$CH(CH_3)$—, —$CH$=$CH$—, —$CH$=$C(CH_3)$—, —$C(CH_3)$=$CH$—, —$C(CH_3)$=$C(CH_3)$—, —$C(C_6H_5)$=$CH$— or —$C(C_6H_5)$=$C(CH_3)$—; furthermore especially —$CH_2$—$CH(C_6H_5)$—, —$CH(CH_3)$—$CH(C_6H_5)$—, —$CHOH$—$CH(C_6H_5)$—, —$C(CH_3)(OH)$—$CH(C_6H_5)$—, —$CH_2$—$CHOH$—, —$CH_2$—$C(CH_3)(OH)$—, —$CH_2$—$C(C_6H_5)(OH)$—, —$CH(CH_3)$—$CHOH$—, —$CH(CH_3)$—$C(CH_3)(OH)$, —$CH(CH_3)$—$C(C_6H_5)(OH)$—, —$CH(C_6H_5)$—$CHOH$—, —$CH(C_6H_5)$—$C(CH_3)(OH)$—, —$CH$=$CH(C_6H_5)$— or —$C(CH_3)$=$C(C_6H_5)$.

Z preferably is amino, methylamino, ethylamino, dimethylamino, diethylamino, imidazol-1-yl or 1,2,4-triazol-1-yl, furthermore, preferably pyrrolidino, piperidino, 4-methylpiperidino or morpholino.

The parameter n preferably has the value 1 or 2, especially 1.

Consequently, the subject of this invention is especially those compound of formula I in which at least one of R, A and Z or the parameter n has one of the above-give preferred meanings. Some of the preferred groups of compounds can be expressed by the following partial formulae Ia-Ih which correspond to formula I and wherein the residues not more precisely defined are defined as in formula I but wherein in Ia $R^5$ is alkyl of 1-6 carbon atoms or cycloalkyl of 3-7 carbon atoms;

in Ib A is $-CR^3(OH)-CHR^4-$, $-CHR^3-CR^4(OH)-$ or $-CR^3=CR^4-$;

in Ic A is $-CR^3=CR^4$;

in Id Z is $-NR^1R^2$ or 1,2,4-triazol-1-yl;

in Ie A is $-CR^3=CR^4-$ and Z is 1-imidazolyl;

in If R is 2-dibenzothienyl;

in Ig R is p-phenylthio-phenyl, p-(2,4-dichlorobenzylthio)-phenyl, p-isopentylthiophenyl, p-cyclohexylthiophenyl or 2-dibenzothienyl; A is $-CH_2-CH_2$, $-CH_2-CH(CH_3)-$, $-CH(CH_3)-CH_2-$, $-CH(CH_3)-CH(CH_3)-$, $-CH(C_6H_5)-CH_2-$, $-CH(C_6H_5)-CH(CH_3)-$, $-CH=CH-$, $-CH=C(CH_3)-$, $-C(CH_3)=CH-$, $-C(CH_3)=C(CH_3)-$, $-C(C_6H_5)=CH-$ or $-C(C_6H_5)=C(CH_3)-$; Z is amino, methylamino, ethylamino, dimethylamino, diethylamino, 1-imidazolyl or 1,2,4-triazol-1-yl; and n is 1 or 2, but wherein R is p-isopentylthiophenyl, p-cyclohexylthiophenyl or 2-dibenzothienyl when A is $-CH_2-CH_2-$ or $-CH(CH_3)-CH_2-$ and Z is 1-imidazolyl;

in Ih R is p-phenylthiophenyl or p-isopentylthiophenyl; A is $-CH=CH$, $-C(CH_3)=CH-$ or $-CH=C(CH_3)-$; Z is dimethylamino, diethylamino or 1-imidazolyl; and n is 1 or 2.

Furthermore, the subject of this invention is a process for the preparation of the compounds of formula I, as well as of their physiologically acceptable acid-addition salts, comprising (a) testing with a reducing agent a compound of formula II $$R-Q \qquad \qquad II$$

wherein Q is a residue reducible to the group $-A-(CH_2)_n-Z$ and R, A, Z and n have the above-given definitions; (b) treating with a solvolyzing agent a compound which corresponds to formula I but wherein the amino and/or hydroxyl group is present in functionally modified form; (c) reacting a compound of formula III $$R-A-(CH_2)_n-X \qquad \qquad III$$

wherein X is Cl, Br, I, OH or a reactive, functionally modified OH and R, A and n have the above-given definitions, with a compound of the formula H-Z or a reactive derivative thereof; (d) and/or treating a hydroxyl-containing compound of formula I [A= $-CR^3(OH)-CHR^4-$ or $-CHR^3-CR^4(OH)$] with a dehydrating agent; (e) and/or treating a compound of formula I [A= $-CR^3(OH)-CHR^4-$, $-CHR^3-CR^4(OH)$ or $-CR^3=CR^4-$] with a reducing agent; (f) and/or changing the residue Z in a compound of formula I, by treatment with an alkylating agent, into another residue Z; (g) and/or converting a base of formula I, by treatment with an acid, into one of its physiologically acceptable acid-addition salts.

Such preparations of the compounds of the formula I are conducted according to per se known methods such as are described in the literature (e.g., in standard works, such as Houben-Weyl, *Methoden der organischen Chemie*, Georg Thieme-Verlag, Stuttgart), namely, under the conditions suitable and known for these reactions.

Thus, use can be made of per se known variants not mentioned in detail herein.

In all formulae given hereinbefore and hereinafter, R, A, Z and n are as defined in formula I unless expressly stated to the contrary.

The starting materials for the preparation of the compounds of formula I are in part known. All can be prepared according to per se known processes. If desired, the starting materials can also be formed in situ in such a manner that they are not isolated from the reaction mixture but rather are immediately further reacted to the compounds of formula I.

The compounds of formula I are obtainable, for example, by reduction of the compounds of formula II. In particular, the primary amines of formula I ($Z=NH_2$) and the secondary alcohols of formula I ($A= -CHOH-CHR^4-$ or $-CHR^3-CHOH-$) can, with advantage, be so prepared.

Insofar as primary amines are to be prepared, in the compounds of formula II the residue Q preferably is the group $-A-(CH_2)_{n-1}-Y$, wherein Y is CN, $CONR^1R^2$, $CH_2NO_2$, $CH_2N_3$, $CH_2NR^1-W$ (wherein W is a benzyl group or another residue which can be split off hydrogenolytically), $CH_2N(W)_2$, $CH=NOH$, $CHOH-NR^1R^2$, $CH=NR^1$, $CH_2NR^6$ (wherein $R^6$ is an alkylidene group of 1-4 carbon atoms, an oxoalkylene group of 4-7 carbon atoms or an oxo-3-oxapentylmethylene group) or another residue which can be reduced to the $CH_2-NR^1R^2$ group. The secondary alcohols of formula I ($A= -CHOH-CHR^4-$ or $-CHR^3-CHOH-$) are preferably obtained by reduction of the corresponding ketones of formula II [Q= $-CO-CHR^4-R^7$, $-(CHR^3)CO-R^7$ or $-CO-CR^4=CH-(CH_2)_{n-1}-Z$, wherein $R^7$ is $-(CH_2)_{n-1}-Y$ or $-(CH_2)_n-Z$]. Furthermore, the group Q can be, for example: $-CR^8-CHR^4-R^7$ (wherein $R^8$ is an alkylidene group of 1-4 carbon atoms or an H atom and an alkenyl group of up to 4 carbon atoms), $-CHR^3-CR^8-R^7$, $-CR^8-CR^8-R^7$, $-CR^3(OH)-CR^8-R^7$, $-CR^8-CR^4(OH)-R^7$, $-CHR^3-CR^4=CH-(CH_2)_{n-1}-Z$, $-CR^3=CR^4-(CH_2)_{n-1}-Y$ or $-CR^7-CR^4=CH-(CH_2)_{n-1}-Z$.

As a rule, the starting materials of formula II are new; however, all can be prepared in analogy to known processes.

Thus, ketonitriles of the formula $R-CO-CHR^4-CN$ are obtainable, e.g., by Friedel-Crafts acylation of the thioethers of the formula R—H with acid chlorides of the formula $Cl-CO-CH_2R^4$ to ketones of the formula $R-CO-CH_2R^4$, followed by subsequent bromination and reaction with KCN. Reduction of these ketonitriles with $NaBH_4$ (or reaction with calculated amounts of the organo-metallic compounds of the formula $R^3-M$, wherein M is Li, MgBr or MgCl and $R^3$ is not H) leads to the hydroxynitriles of the formula $R-CR^3(OH)-CHR^4-CN$, from which, by dehydration, there can be obtained the unsaturated nitriles of the formula $R-CR^3=CR^4-CN$; by hydrolysis, the hydroxy acids of the formula $R-CR^3(OH)-CHR^4-COOH$; by the dehydration thereof, the unsaturated acids of the formula $R-CR^3=CR^4-COOH$; and by the reduction thereof, the saturated acids of the formula R—CHR$^3$—CHR$^4$COOH. Ketones of the formula R—CO—CHR$^4$—(CH$_2$)$_n$—Z are, e.g., preparable by Friedel-Crafts acylation of the thioethers of the formula R—H with acid chlorides of the formulae Cl—CO—CHR$^4$—(CH$_2$)$_n$—Cl or Cl—CO—CHR$^4$—(CH$_2$)$_n$—Z and, if necessary, subsequent reaction of the chloroketones obtained of the formula R—CO—CHR$^4$—(CH$_2$)$_n$—Cl with bases of the formula HZ. Acid amides of the formula R—CR$^3$(OH)—CHR$^4$—CO—Z are, e.g., obtainable by Friedel-Crafts acylation or by Gattermann or Vilsmeier reaction of the thioethers of the formula R—H to ketones or aldehydes of the formula R—CO—R$^3$, Reformatski reaction with esters of the formula Br—CHR$^4$—COOC$_2$H$_5$ to hydroxy esters of the formula R—CR$^3$(OH)—CHR$^4$—COOC$_2$H$_5$ and reaction with bases of the formula HZ. Splitting off of water leads to unsaturated amides of the formula R—CR$^3$=CR$^4$—CO—Z and reduction leads to saturated amides of the formula R—CHR$^3$—CHR$^4$—CO—Z. Reduction of the said hydroxyesters with HI leads, with simultaneous saponification, to acids of the formula R—CHR$^3$—CHR$^4$—COOH, which can be converted with LiAlH$_4$ into the corresponding alcohols of the formula R—CHR$^3$—CHR$^4$—CH$_2$OH. Diols of the formula R—CR$^3$(OH)—CHR$^4$—CH$_2$OH are obtainable by reduction of the above-mentioned hydroxyesters with LiAlH$_4$ and alcohols of the formula R—CR$^3$=CR$^4$—CH$_2$OH are obtainable by dehydration and subsequent reduction of the hydroxyesters. From the mentioned alcohols there can be prepared in the usual manner, e.g., with SOCl$_2$ or PBr$_5$, the corresponding halides which can be converted with alkali metal nitrites into the corresponding nitro compounds of the formula R—A—CH$_2$NO$_2$; with alkali metal azides into the azides of the formula R—A—CH$_2$N$_3$; and with amines of the formula W—NH$_2$ (e.g., benzylamine) or (W)$_2$NH into the amines of the formula R—A—CH$_2$—NH—W or R—A—CH$_2$N(W)$_2$. Oxidation of the alcohols leads to the corresponding aldehydes of the formula R—A—CHO which can be converted with hydroxylamine into the corresponding oximes of the formula R—A—CH=NOH and with a base of the formula HZ into the corresponding aldehyde-ammonias of the formula R—A—CHOH-Z or imines of the formula R—A—CH=NR$^1$. Unsaturated nitriles of the formula R—CR$^3$=CH—CN are also preparable from the mentioned carbonyl compounds of the formula R—CO—R$^3$ and cyanoacetic acid. Reduction of the carbonyl compounds of the formula R—CO—R$^3$ yields the corresponding alcohols of the formula R—CHR$^3$—OH which, via the corresponding bromides of the formula R—CHR$^3$—Br, can easily be converted into the nitriles of the formula R—CHR$^3$—CN. Reaction with organometallic compounds of the formula CH$_3$M and hydrolysis yields ketones of the formula R—CHR$^3$—CO—CH$_3$ which, by bromination and subsequent reaction with a base of the formula HNR$^1$R$^2$, can be converted into the aminoketones of the formula R—CHR$^3$—CO—CH$_2$—NR$^1$R$^2$.

Of the starting materials of formula II, the ketones of the formula R—CO—CHR$^4$—(CH$_2$)$_n$—Z, furthermore the amides of the formula R—A—CO—Z and the nitriles of the formula R—A—CN are preferred.

The starting materials of formula II can be converted into the compounds of formula I for example by catalytic hydrogenation, with nascent hydrogen, with complex metal hydrides or with the help of other chemical reducing agents. The most suitable reduction methods for the individual starting materials are, in general, dependent upon the nature of the functional group Y and are wellknown to a person skilled in the art according to the statements in the literature and fully conventional considerations. Thus, e.g., nitriles, amines of the formula R—A—(CH$_2$)$_n$—NH—W or R—A—(CH$_2$)$_n$—N(W)$_2$, oximes and aldehyde-ammonias can be especially advantageously catalytically hydrogenated. A reduction of the acid amides, on the other hand, takes place especially advantageously with complex metal hydrides or with diborane.

For catalytic hydrogenations, there are suitable, for example, noble metals, nickel and cobalt catalysts, and furthermore, also mixed catalysts, such as copper chromoxide. As noble metals, there are suitable platinum and palladium, which can be present on carriers (e.g., on charcoal, calcium carbonate or strontium carbonate), as oxides (e.g., platinum oxide) or in finely divided form. Nickel and cobalt catalysts are expediently used as Raney metals. One can expediently hydrogenate at pressures between about 1 and 200 atm and at temperatures between about −80° and +150°, preferably between 20° and 100°. The hydrogenation takes place in the presence of an inert solvent, e.g., of an alcohol, such as methanol, ethanol or isopropanol, of a carboxylic acid, such as acetic acid, of an ester, such as ethyl acetate, of an ether, such as tetrahydrofuran (THF) or dioxane. One can also use solvent mixtures, e.g., also water-containing mixtures. Furthermore, it can be advantageous to add thereto a base, such as sodium or potassium hydroxide or ammonia, in the case of the hydrogenation, e.g., in the case of the hydrogenation of nitriles.

Furthermore, as reducing agents, there can be used complex metal hydrides, such as LiAlH$_4$, NaBH$_4$ or NaAl(OCH$_2$CH$_2$OCH$_3$)$_2$H$_2$, as well as diborane, if desired, with the addition of catalysts, such as BF$_3$, AlCl$_3$ or LiBr. As solvents, there are suitable for this purpose especially ethers, such as diethyl ether, THF, dioxane, 1,2-dimethoxyethane or diglyme, as well as hydrocarbons, such as benzene. The reduction of ketones is preferably carried out with NaBH$_4$; for this purpose, in the first place there are suitable, as solvent, alcohols, such as methanol or ethanol, or mixtures of these alcohols with THF. According to this method, the reduction is preferably conducted at temperatures between about −80° and +150°, especially between about 20° and 120°.

Furthermore, the reaction with nascent hydrogen is suitable as a reduction method. This can be produced, for example, by treatment of metals with acids or bases. Thus, e.g., the systems zinc/acid, zinc/aqueous alkali metal hydroxide solution, iron/acid or tin/acid can be used. As acids, there are suitable, e.g., hydrochloric acid or acetic acid. An alkali metal, such as sodium, in an alcohol, such as ethanol, isopropanol, n-butanol, amyl alcohol, isoamyl alcohol or in phenol, can also be used as reducing agent, furthermore, e.g., an aluminum-nickel alloy in aqueous alkaline or aqueous alcoholic alkaline solution, as well as sodium or aluminum amalgam in aqueous alcoholic or aqueous solution. In the case of these methods, the reaction temperatures lie between about 0° and about 150°, preferably between about 20° and 120°.

The starting compounds of formula II can also be converted into compounds of formula I by cathodic reduction, expediently in aqueous alcoholic or aqueous acetic acid medium. Further suitable reducing agents are, for example, sodium dithionite in aqueous alcoholic or alkaline solution, furthermore iron(II) hydroxide, tin(II) chloride, hydrogen sulphide, hydrogen sulphides, sulphides, polysulphides, hydrazine, all of which are used according to the conditions given in the literature for such reductions.

By suitable choice of the reagent and reaction conditions, selective reductions are also possible. Thus, Schiff bases R—CR$^3$=CR$^4$—CH=NR$^1$ or R—CR$^3$=C-R$^4$—(CH$_2$)$_n$—N=alkyl— idenes (wherein the alkylidene group possesses 1-4 C-atoms) can be reduced with LiAlH$_4$ to the corresponding unsaturated amines.

Furthermore, the compounds of formula I are obtainable by solvolysis, preferably hydrolysis, of starting materials but wherein the amino and/or the hydroxyl group is present in functionally changed form.

The starting materials for the solvolysis are, as a rule, new but can be prepared in analogy to per se known methods.

Such starting materials, in particular, include e.g. acyl derivatives of the amines of formula I, especially of the amides of the formula R—A—(CH$_2$)$_n$—NR$^1$—Ac (wherein Ac is any desired acyl radical, the nature of which is not critical since it is split off in the case of the solvolysis but which preferably possesses 1-10 C-atoms, e.g. alkanoyl, aroyl, alkyl-sulphonyl or aryl-sulphonyl with, in each case, up to 10 C-atoms, e.g. acetyl, benzoyl, methanesulphonyl or p-toluene-sulphonyl). These amides are obtainable e.g. by Friedel-Crafts alkylation of the thioesters of the formula R—H with halo-amides of the formula Cl—A—(CH$_2$)$_n$—NR$^1$—Ac or Br—A-(CH$_2$)$_n$—NR$^1$-Ac.

Preferred starting materials for the solvolysis in which the OH group is functionally changed correspond e.g. to the general formula IV R—E—(CH$_2$)$_n$—Z    IV wherein E is —CR$^3$L—CHR$^4$— or CHR$^3$—CR$^4$L— and L is a functionally changed OH group, especially OM or OAc.

These compounds are, e.g., the corresponding alcoholates, especially the magnesium or lithium alcoholates, such as result as reaction products in the case of Grignard reactions or in the case of reactions with organo-lithium compounds; and the esters (e.g. the carboxylic acid esters, whereby the carboxylic acid residue preferably possesses up to 7 C-atoms, e.g. acetyl or benzoyl, the alkyl- or aryl-sulphonic acid esters, wherein the alkyl radical preferably contains 1-6, the aryl radical preferably 6-10 C-atoms); furthermore, the ethers (e.g. the alkyl ethers, wherein the alkyl group preferably contains up to 6 C-atoms, the aryl ethers, wherein the aryl group preferably contains 6-10 C-atoms, and the aralkyl ethers, wherein the aralkyl group preferably possesses 7-11 C-atoms); and the boric acid esters which result as intermediates in the case of the hydroboration. Furthermore, in place of the hydroxyl group, there can be a chlorine, bromine or iodine atom; there are then present the corresponding hydrohalic acid esters.

The mentioned magnesium or lithium alcoholates are obtainable e.g. by reaction of the above-mentioned ketones of the formula R—CO—CHR$^4$—(CH$_2$)$_n$—Z with organo-metallic compounds of the formula R$^3$—M (wherein R$^3$ is not H) or by reaction of organo-metallic compounds of the formula R—M with ketones of the formula R$^3$—CO—CHR$^4$—(CH$_2$)$_n$—Z or by reaction of carbonyl compounds of the formula R—CO—R$^3$ with organo-metallic compounds of the formula M—CHR$^4$—(CH$_2$)$_n$—Z, expediently in an ether, such as diethyl ether or THF as solvent. Halides of the formula R—CR$^3$Cl—CHR$^4$—(CH$_2$)$_n$—Z or R—CR$^4$Br—CHR$^4$—(CH$_2$)$_n$—Z can be prepared e.g. by halogenation of acid amides of the formula R—A—(CH$_2$)$_{n-1}$—COZ and subsequent reduction with LiAlH$_4$. From the halides are preparable the corresponding esters of the formula R—CR$^3$(OAc)—CHR$^4$—(CH$_2$)$_n$—Z by reaction with potassium acylates, e.g. potassium acetate.

The solvolysis of these compounds preferably takes place by the action of a solvent, such as water (hydrolysis), or of an alcohol with preferably 1-4 C-atoms (alcoholysis) in the presence of an acidic or basic catalyst, e.g. of a mineral acid, such as sulphuric acid or hydrochloric acid, or a metal hydroxide, such as sodium, potassium, calcium, barium, lead or silver hydroxide, or of a metal or ammonium salt, such as sodium or potassium carbonate or ammonium chloride. As alcohols, there preferably are used methanol, ethanol or isopropanol but one can also employ mixtures of water with one of these alcohols. The solvolysis expediently takes place at temperatures between about 0° and about 120°.

In particular, the mentioned amides are expediently hydrolysed by boiling for several hours with aqueous, aqueous alcoholic or alcoholic hydrochloric acid, sulphuric acid, aqueous sodium hydroxide solution or potassium hydroxide solution. The mentioned magnesium alcoholates are expediently not isolated but rather, after their formation in the Grignard reaction, hydrolysed in situ with dilute acids, e.g. sulphuric acid or hydrochloric acid, or with dilute ammonium chloride solution. The mentioned halides and esters are preferably saponified in aqueous or aqueous alcoholic solution or suspension, whereby, if desired, a solubilizing agent can be present, e.g. an alcohol, glycol or glycol ether. As saponification agents, there preferably are used alkalis, such as NaOH or KOH.

Furthermore, the compounds of the formula I are obtainable by reaction of a compound of the formula R—A—(CH$_2$)$_n$—X (III) with a compound of the formula H—Z or a reactive derivative of such a compound. The starting materials of the formula III can be prepared e.g. by reduction of ketones of the formula R—CO—CHR$^4$—(CH$_2$)$_n$—X or by reaction of these ketones with organo-metallic compounds of the formula R$^3$—M (wherein R$^3$ is not H) and subsequent hydrolysis of carbinols of the formula R—CR$^3$(OH)—CHR$^4$—(CH$_2$)$_n$—X and, if desired, subsequent dehydration and/or reduction. The starting materials of the formula H—Z are known.

The reaction of compounds of formula III with compounds of the formula H—Z expediently takes place at temperatures between about 0° and about 250°, preferably about 50° and 120°, and at pressures between about 1 and about 50 atm. The reaction can be conducted in the presence of an inert solvent, e.g. of an alcohol, such as methanol, ethanol, isopropanol, n-butanol, or an ether, such as diethyl ether, diisopropyl ether, THF, dioxane, of a hydrocarbon, such as benzene, toluene, xylene, of an amide, such as dimethylformamide (DMF), or a sulphoxide, such as dimethyl sulphoxide. If desired, a catalyst can be present, e.g. sodium amide, which can also be produced in situ from sodium and liquid ammonia, furthermore, bases, such as sodium carbonate, potassium carbonate, sodium bicarbonate or potassium bicarbonate. It is also possible to use an excess of the compound of the formula H—Z as solvent, expediently at the boiling temperature. X preferably is Cl, Br or I. If X is a reactive functionally changed OH group, then it preferably is an alkyl- or aryl-sulphonyloxy group with especially up to 10 C-atoms. Secondary amines of the formula R—A—(CH$_2$)$_n$—NHR$^1$ (wherein R' is alkyl with 1–4 C-atoms) can also be prepared by heating alcohols of the formula R—A—(CH$_2$)$_n$—OH with alkylamines of the formula R$^1$—NH$_2$ in the presence of Raney nickel.

If desired, a hydroxy compound obtained of the formula R—CR$^3$(OH)—CHR$^4$—(CH$_2$)$_n$—Z or R—CHR$^3$—CR$^4$(OH)—(CH$_2$)$_n$—Z can be dehydrated to the corresponding unsaturated compounds of the formula R—CR$^3$=CR$^4$—(CH$_2$)$_n$—Z, expediently by the action of an acidic catalyst, such as hydrochloric acid, sulphuric acid or a sulphonic acid, such as p-toluene-sulphonic acid, in an inert solvent, e.g. a hydrocarbon, such as benzene or toluene, at temperatures between about 0° and about 150°, preferably between 80° and 110°. For the dehydration of secondary alcohols, there preferably are used dilute aqueous ethanolic hydrochloric acid at about 70°–80°, for the dehydration of tertiary alcohols. However, 20% aqueous hydrochloric acid, also with-the addition of dioxane, can be used at 90°–100°. In the case of the dehydration, as a rule, there are formed the (more stable) trans forms (or E-forms) of the compounds of formula I (A=—CR$^3$=CR$^4$—).

Furthermore, if desired, there can be reduced the abovementioned hydroxy compounds of the formulae R—CR$^3$(OH)—CHR$^4$—(CH$_2$)$_n$—Z or R—CHR$^3$—CR$^4$(OH)—(CH$_2$)$_n$—Z and the unsaturated compounds of the formula R—CR$^3$=CR$^4$—(CH$_2$)$_n$—Z to the saturated compounds of the formula R—CHR$^3$—CHR$^4$—(CH$_2$)$_n$—Z. The reduction of the hydroxy compounds takes place e.g. with hydriodic acid, preferably in acetic acid, at temperatures between 20° and (preferably) boiling temperature. The unsaturated compounds can be preferably catalytically hydrogenated under the abovementioned conditions, for example on a noble metal catalyst, such as palladium on charcoal, at room temperature and normal pressure.

Furthermore, in a compound obtained of formula I, the residue Z can be changed by alkylation into another residue Z.

Thus, a primary (I, Z=NH$_2$) or secondary amine (I, Z=NHAlkyl) obtained can be converted, by treatment with alkylating agents, into a secondary or tertiary amine of formula I. As alkylating agents, there are suitable, according to the invention, e.g. compounds of the formulae R$^1$—X, R$^2$—X, or possibly X—R$^1$R$^2$—X, e.g. methyl chloride, methyl bromide, methyl iodide, dimethyl sulphate, p-toluene-sulphonic acid methyl ester, ethyl chloride, ethyl bromide, ethyl iodide, diethyl sulphate, n-propyl chloride, bromide or iodide etc., but also 1,4-dichlorobutane, 1,4-dibromobutane, 1,4-diiodobutane, 1,5-dichloro-, 1,5-dibromo- or 1,5-diiodopentane, 2,2'-dichloro, 2,2'-dibromo- or 2,2'-diiododiethyl ether. Furthermore, these can be condensed with aldehydes or ketones with the formation of aldehyde-ammonia compounds or Schiff bases and subsequently hydrogenated as stated above or treated with an alkylation agent followed by subsequent hydrolysis of the quaternary salt obtained. For example, a primary amine can be converted by condensation with benzaldehyde into the N-benzylidene compound and this can be converted with an alkyl halide into one of its quaternary salts which subsequently, e.g. by treatment with aqueous alcohol, can be converted into the secondary amine with splitting off of benzaldehyde. Furthermore, alkylation with aldehydes or ketones under reducing conditions can be used, whereby, as intermediate product the corresponding aldehyde-ammonia result. For example, one or two methyl groups can be introduced with formaldehyde in the presence of formic acid. Furthermore, alkylation with an alcohol which possesses 1–4 C-atoms can be performed in the presence of Raney nickel. The alkylation is expediently undertaken in the presence or absence of one of the mentioned inert solvents, at temperatures between about 0° and about 120°, preferably between 40° and 100°, whereby a catalyst can also be present, preferably a base, such as potassium tert-butylate.

A base obtained of formula I can be conventionally converted with an acid into the related acid-addition salt. For this reaction, there are suitable acids which provide physiologically acceptable salts. Thus, inorganic acids can be used, e.g. sulphuric acid, hydrohalic acids, such as hydrochloric acid or hydrobromic acid, phosphoric acids, such as orthophosphoric acid, nitric acid, sulphamic acid, furthermore organic acids, in particular aliphatic, alicyclic, araliphatic, aromatic or heterocyclic mono- or polybasic carboxylic, sulphonic or sulphuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- and ethane-sulphonic acid, ethane-disulphonic acid, 2-hydroxyethane-sulphonic acid, benzenesulphonic acid, p-toluene-sulphonic acid, naphthalene-mono- and disulphonic acids and laurylsulphuric acid.

The free bases of formula I can, if desired, be liberated from their salts by treatment with strong bases, such as sodium or potassium hydroxide, sodium or potassium carbonate.

The compounds of formula I can contain one or more centers of asymmetry. In this case, they are usually present in racemic form. Racemates obtained can be separated according to per se known methods mechanically or chemically into their optical antipodes. Preferably, from the racemic mixture, diastereomers are formed by reaction with an optically-active separation agent. As separation agents, there are suitable e.g. optically-active acids, such as the D- and L- forms of tartaric acid, diacetyl-tartaric acid, dibenzoyltartaric acid, mandelic acid, malic acid, lactic acid or the various optically-active camphor-sulphonic acid, such as β-camphor-sulphonic acid.

Naturally, it is also possible to obtain optically-active compounds of the formula I according to the abovedescribed methods by using starting materials which are already optically active.

It has been found that the compounds of formula I, in the case of good compatibility, possess valuable pharmacological properties in mammals; including humans. In particular, antimycotic and anti-bacterial actions occur, for example against *Microsporum audouini*, Dermophytes, such as *Trichophyton rubrum* and *Trichophyton mentagrophytes*, *Histoplasma capsulatum*, *Aspergillus fumigatus*, yeasts, such as *Candida albicans*, *Nocardia asteroides*, *Staphylococcus aureus*, *Streptococcus pyogenes*, *Proteus vulgaris*, *Pseudomonas aeruginosa*, *Mycobacterium ranae* and/or *Escherichia coli*. The compounds also act against systemic fungal infections; furthermore, actions occur against Protozoa, especially against Trichomonads.

These activities can be determined e.g. according to the usual agar dilution method in vitro but also in vivo, for example on mice, rats and rabbits.

Furthermore, they display antiphlogistic actions which can be demonstrated e.g. in the adjuvant arthritis test according to the method for Newbould (Brit. J. Pharmacol. 21 (1963) pages 127-136) on rats. Furthermore, they display anti-arteriosclerotic, cholesterol level-sinking (detectable in the serum of rats according to the method of Levine et al., Automation in Analytical Chemistry, Technicon Symposium 1967, Mediad, New York, pages 25-28) and triglyceride level-sinking actions (detectable according to the method of Noble and Campbell, Clin. Chem. 16 (1970) pages 166-170). Furthermore, there can be observed analgesic, antipyretic, enzyme-inducing, fibrinolytic and thrombocyte aggregation-inhibiting action according to methods conventional for this purpose.

The compounds of the formula I and their physiologically acceptable acid-addition salts can, therefore, be used as medicinally active materials and also as intermediate products for the preparation of other medicinally active materials.

Furthermore, the subject of the invention is the use of new compounds of formula I and of their physiologically acceptable acid-addition salt for the preparation of pharmaceutical compositions, especially in non-chemical ways. They can hereby be brought into a suitable dosage form, together with at least one solid, liquid and/or semiliquid carrier or adjuvant and possibly together with one or more further active materials.

Furthermore, the invention involves agents, especially pharmaceutical compositions, containing a compound of the formula I and/or one of its physiologically acceptable acid-addition salts.

These compositions can be used as medicaments in human and veterinary medicine. As carrier materials, there are suitable organic or inorganic substances which are especially suitable for topical but also for enteral (e.g. oral) or parenteral administration and which do not react with the new compounds, for example, water, vegetable oils, hydrocarbons, such as alkylated naphthalenes, halogenated hydrocarbons, such as $CF_2Cl_2$ (e.g. for aerosols), benzyl alcohols, polyethylene glycols, glycerol triacetate, gelatine, carbohydrates, such as lactose or starch, magnesium stearate, talc or vaseline. For oral use, there serve especially tablets, dragees, capsules, syrups, juices, or drops; for rectal use suppositories; for intravaginal use, ovules; for parenteral use, solutions, preferably oily or aqueous solutions, furthermore suspensions, emulsions or implants, for topical use, solutions, lotions, emulsions, sprays (aerosols), salves, creams, pastes or powders. The new compounds can also be lyophilised and the lyophilisates obtained used e.g. for the preparation of injection preparations. The mentioned compositions can be sterilized amd/or contain adjuvant materials, such as lubricating, preserving, stabilizing and/or wetting agents, emulsifiers, salts for the influencing of the osmotic pressure, buffer substances, coloring, flavoring and/or aroma generating materials. If desired, they can also contain one or more other active materials, e.g one or more antibiotics, vitamins and/or other antimycotics.

As a rule, the new compounds are administered in analogy to known antimycotics commercially available (e.g. clotrimazole or miconazole). In the case of the preferred topical administration in combination with carrier materials suitable therefore, a high activity can be ascertained over a wide range of dilution. For example, concentrations of the active material between about 0.1 and 10 weight percent, referred to the weight of the preparation used, show themselves to be effective for the combatting of fungi or bacteria. Concentrations of about 1 to 3 weight percent are preferred.

Insofar as the new compounds are used as anti-phlogistic or lipid sinkers, their oral administration is preferred. As a rule, they are then administered in analogy to known anti-phlogistics (e.g. indomethacine) or lipid sinkers (e.g. clofibrate), preferably in dosages between about 5 and 500 mg, especially between 20 and 200 mg per dosage unit. The daily dosage preferably lies between about 0.2 and 20 mg/kg of body weight. However, the special dose for each patient depends upon the conventional most varied factors, e.g. upon the effectiveness of the special compound employed, upon the age, body weight, general state of health, sex and diet of the host, upon the time of administration and its route, upon the rate of excretion, upon medicinal combination and upon severity of the disease in question. Thus, in individual cases, higher or lower concentrations or dosages than those mentioned can be employed.

For the other utilities of the compounds of this invention, the following dosage units are suitable. Also included in the table are compounds having the same utilities which may be used as a guide in the administration of the thioethers of this invention.

| ACTIVITY | DOSAGE UNIT MG | ADMINISTRATION ANALOGOUS TO: |
|---|---|---|
| Analgesic | 5–500 | metamizol |
| Antipyretic | 5–500 | metamizol |
| Enzyme-inducing | 5–500 | phenobarbital |
| Thrombocyte aggreagation inhibiting | 5–500 | acetylsalicylic acid |

Each of the compounds of formula I mentioned in the following Examples is especially suitable for the preparation of pharmaceutical compositions.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the following Examples, the phrase "usual working up" means: there is added to the material involved, if necessary, water or dilute aqueous sodium hydroxide solution; it is extracted with an organic solvent which is not miscible with water (e.g., benzene, chloroform or dichloromethane); the organic phase is separated off and dried over sodium sulphate; and it is filtered, evaporated and purified by chromatography and/or crystallization. The product can also be purified by crystallization of one of its acid-addition salts.

EXAMPLE 1

To a suspension of 7.6 g of $LiAlH_4$ in 250 ml of absolute THF, there is added dropwise, with stirring, a solution of 25.1 g of 3-p-isopentylthiophenyl-propionamide [obtainable by Friedel-Crafts acetylation of phenyl-isopentyl sulphide to give p-isopentylthioacetophenone (b.p. 198°–201°/18 mm), bromination to give p- isopentylthiophenacyl bromide (oil), reaction with KCN in DMF to give p-isopentylthiophenacyl cyanide (m.p. 62°-63°), reduction with NaBH₄ to give 3-p-isopentylthiophenyl-3-hydroxypropionitrile, hydrolysis with simultaneous splitting off of water to give p-isopentylthiocinnamic acid (m.p. 132°-133°), reduction with Na amalgam to give 3-p-isopentylthiophenylpropionic acid, reaction with SOCl₂ to give the chloride and reaction with NH₃ in 500 ml of THF. The mixture is boiled for 16 hours, mixed, while cooling, with ethyl acetate, then with 32% aqueous sodium hydroxide solution and worked up as usual to obtain 3-p-isopentylthiophenyl-propylamine. Hydrochloride m.p. 193° (decomposition).

EXAMPLES 2 to 34

Analogously to Example 1, from the corresponding amides there are obtainable:

2. 3-p-phenylthiophenyl-propylamine.
3. 3-p-phenylthiophenyl-butylamine.
4. 3-p-phenylthiophenyl-2-methyl-propylamine.
5. 3-p-phenylthiophenyl-2-methyl-butylamine.
6. 3-p-phenylthiophenyl-3-phenyl-propylamine.
7. 3-p-phenylthiophenyl-2-methyl-3-phenyl-propylamine.
8. 4-p-phenylthiophenyl-butylamine.
9. 4-p-phenylthiophenyl-pentylamine.
10. 5-p-phenylthiophenyl-pentylamine.
11. 5-p-phenylthiophenyl-hexylamine.
12. 3-p-(2,4-dichlorobenzylthio)-phenyl-propylamine.
13. 3-p-(2,4-dichlorobenzylthio)-phenyl-butylamine.
14. 3-p-(2,4-dichlorobenzylthio)-phenyl-2-methyl-propylamine.
15. 3-p-(2,4-dichlorobenzylthio)-phenyl-2-methyl-butylamine.
16. 3-p-(2,4-dichlorobenzylthio)-phenyl-3-phenyl-propylamine.
17. 3-p-(2,4-dichlorobenzylthio)-phenyl-2-methyl-3-phenyl-propyl-amine.
18. 3-p-isopentylthiophenyl-butylamine.
19. 3-p-isopentylthiophenyl-2-methyl-propylamine.
20. 3-p-isopentylthiophenyl-2-methyl-butylamine.
21. 3-p-isopentylthiophenyl-3-phenyl-propylamine.
22. 3-p-isopentylthiophenyl-2-methyl-3-phenyl-propylamine.
23. 3-p-cyclohexylthiophenyl-propylamine.
24. 3-p-cyclohexylthiophenyl-butylamine.
25. 3-p-cyclohexylthiophenyl-2-methyl-propylamine.
26. 3-p-cyclohexylthiophenyl-2-methyl-butylamine.
27. 3-p-cyclohexylthiophenyl-3-phenyl-propylamine.
28. 3-p-cyclohexylthiophenyl-2-methyl-3-phenyl-propylamine.
29. 3-(2-dibenzothienyl)-propylamine.
30. 3-(2-dibenzothienyl)-butylamine.
31. 3-(2-dibenzothienyl)-2-methyl-propylamine.
32. 3-(2-dibenzothienyl)-2-methyl-butylamine.
33. 3-(2-dibenzothienyl)-3-phenyl-propylamine.
34. 3-(2-dibenzothienyl)-2-methyl-3-phenyl-propylamine.

EXAMPLE 35

A solution of 2.49 g of 3-p-isopentylthiophenyl-3-hydroxy-propionitrile in 30 ml of absolute THF is added dropwise, with stirring and passing through of N₂, to a mixture of 0.76 g of LiAlH₄ in 30 ml of absolute THF. This is stirred for an additional 30 minutes at 20°, decomposed with aqueous sodium sulphate solution and worked up as usual to obtain 3-p-isopentylthiophenyl-3-hydroxy-propylamine.

EXAMPLES 36 to 94

Analogously to Example 35, from the corresponding hydroxyamides there are obtained:

36. 3-p-phenylthiophenyl-3-hydroxy-propylamine.
37. 3-p-phenylthiophenyl-2-hydroxy-propylamine.
38. 3-p-phenylthiophenyl-3-hydroxy-butylamine.
39. 3-p-phenylthiophenyl-2-hydroxy-butylamine.
40. 3-p-phenylthiophenyl-2-metyl-3-hydroxy-propylamine.
41. 3-p-phenylthiophenyl-2-methyl-2-hydroxy-propylamine.
42. 3-p-phenylthiophenyl-2-methyl-B 3-hydroxy-butylamine.
43. 3-p-phenylthiophenyl-2-methyl-2-hydroxy-butylamine.
44. 3-p-phenylthiophenyl-3-phenyl-3-hydroxy-proylamine.
45. 3-p-phenylthiophenyl-3-phenyl-2-hydroxy-propylamine.
46. 3-p-phenylthiophenyl-2-methyl-3-phenyl-3-hydroxy-propylamine.
47. 3-p-phenylthiophenyl-2-methyl-3-phenyl-2-hydroxy-propylamine.
48. 3-p-(2,4-dichlorobenzylthio)-phenyl-3-hydroxy-propylamine.
49. 3-p-(2,4-dichlorobenzylthio)-phenyl-2-hydroxy-propylamine.
50. 3-p-(2,4-dichlorobenzylthio)-phenyl-3-hydroxy-butylamine.
51. 3-p-(2,4-dichlorobenzylthio)-phenyl-2-hydroxy-butylamine.
52. 3-p-(2,4-dichlorobenzylthio)-phenyl-2-methyl-3-hydroxypropylamine.
53. 3-p-(2,4-dichlorobenzylthio)-phenyl-2-methyl-2-hydroxypropylamine.
54. 3-p-(2,4-dichlorobenzylthio)-phenyl-2-methyl-3-hydroxybutylamine.
55. 3-p-(2,4-dichlorobenzylthio)-phenyl-2-methyl-2-hydroxybutylamine.
56. 3-p-(2,4-dichlorobenzylthio)-phenyl-2-methyl-3-hydroxypropylamine.
57. 3-p-(2,4-dichlorobenzylthio)-phenyl-2-methyl-2-hydroxypropylamine.
58. 3-p-(2,4-dichlorobenzylthio)-phenyl-3-phenyl-3-hydroxypropylamine.
59. 3-p-(2,4-dichlorobenzylthio)-phenyl-3-phenyl-2-hydroxypropylamine.
60. 3-p-isopentylthiophenyl-2-hydroxy-propylamine.
61. 3-p-isopentylthiophenyl-3-hydroxy-butylamine.
62. 3-p-isopentylthiophenyl-2-hydroxy-butylamine.
63. 3-p-isopentylthiophenyl-2-methyl-3-hydroxy-propylamine.
64. 3-p-isopentylthiophenyl-2-methyl-2-hydroxy-propylamine.
65. 3-p-isopentylthiophenyl-2-methyl-3-hydroxy-butylamine.
66. 3-p-isopentylthiophenyl-2-methyl-2-hydroxy-butylamine.
67. 3-p-isopentylthiophenyl-3-phenyl-3-hydroxy-propylamine.
68. 3-p-isopentylthiophenyl-3-phenyl-2-hydroxy-propylamine.
69. 3-p-isopentylthiophenyl)-2-methyl-3-phenyl-3-hydroxypropylamine.

70. 3-p-isopentylthiophenyl-2-methyl-3-phenyl-2-hydroxypropylamine.
71. 3-p-cyclohexylthiophenyl-3-hydroxy-propylamine.
72. 3-p-cyclohexylthiophenyl-2-hydroxy-propylamine.
73. 3-p-cyclohexylthiophenyl-3-hydroxy-butylamine.
74. 3-p-cyclohexylthiophenyl-2-hydroxy-butylamine.
75. 3-p-cyclohexylthiophenyl-2-methyl-3-hydroxy-propylamine.
76. 3-p-cyclohexylthiophenyl-2-methyl-2-hydroxy-propylamine.
77. 3-p-cyclohexylthiophenyl-2-methyl-3-hydroxy-butylamine.
78. 3-p-cyclohexylthiophenyl-2-methyl-2-hydroxy-butylamine.
79. 3-p-cyclohexylthiophenyl-3-phenyl-3-hydroxy-propylamine.
80. 3-p-cyclohexylthiophenyl-3-phenyl-2-hydroxy-propylamine.
81. 3-p-cyclohexylthiophenyl-2-methyl-3-phenyl-3-hydroxypropylamine.
82. 3-p-cyclohexylthiophenyl-2-methyl-3-phenyl-2-hydroxypropylamine.
83. 3-(2-dibenzothienyl)-3-hydroxy-propylamine.
84. 3-(2-dibenzothienyl)-2-hydroxy-propylamine.
85. 3-(2-dibenzothienyl)-3-hydroxy-butylamine.
86. 3-(2-dibenzothienyl)-2-hydroxy-butylamine.
87. 3-(2-dibenzothienyl)-2-methyl-3-hydroxy-propylamine.
88. 3-(2-dibenzothienyl)-2-methyl-2-hydroxy-propylamine.
89. 3-(2-dibenzothienyl)-2-methyl-3-hydroxy-butylamine.
90. 3-(2-dibenzothienyl)-2-methyl-2-hydroxy-butylamine.
91. 3-(2-dibenzothienyl)-3-phenyl-3-hydroxy-propylamine.
92. 3-(2-dibenzothienyl)-3-phenyl-2-hydroxy-propylamine.
93. 3-(2-dibenzothienyl)-2-methyl-3-phenyl-3-hydroxy-propylamine.
94. 3-(2-dibenzothienyl)-2-methyl-3-phenyl-2-hydroxy-propylamine.

EXAMPLE 95

A solution of 2.49 g of 3-p-isopentylthiophenylcinnamic acid amine (preparable from the acid via the chloride) in 30 ml of benzene is added dropwise, with stirring, to a suspension of 5 g of sodium aluminum bis(2-methoxyethoxy)-dihydride in 30 ml of benzene. This is boiled overnight, cooled, carefully decomposed with water and worked up as usual to obtain 3-isopentylthiophenyl-2-propene-1-amine. Hydrochloride m.p. 193°-195°.

EXAMPLES 96–125

Analogously to Example 95, from the corresponding unsaturated amides there are obtained:
96. 3-p-phenylthiophenyl-2-propen-1-amine.
97. 3-p-phenylthiophenyl-2-buten-1-amine.
98. 3-p-phenylthiophenyl-2-methyl-2-propen-1-amine.
99. 3-p-phenylthiophenyl-2-methyl-2-buten-1-amine.
100. 3-p-phenylthiophenyl-3-phenyl-2-propen-1-amine.
101. 3-p-phenylthiophenyl-2-methyl-3-phenyl-2-propen-1-amine.
102. 3-p-(2,4-dichlorobenzylthio)-phenyl-2-propen-1-amine.
103. 3-p-(2,4-dichlorobenzylthio)-phenyl-2-buten-1-amine.
104. 3-p-(2,4-dichlorobenzylthio)-phenyl-2-methyl-2-propen-1-amine.
105. 3-p-(2,4-dichlorobenzylthio)-phenyl-2-methyl-2-buten-1-amine.
106. 3-p-(2,4-dichlorobenzylthio)-phenyl-3-phenyl-2-propen-1-amine.
107. 3-p-(2,4-dichlorobenzylthio)-phenyl-2-methyl-3-phenyl-2-propen-1-amine.
108. 3-p-isopentylthiophenyl-2-buten-1-amine.
109. 3-p-isopentylthiophenyl-2-methyl-2-propen-1-amine.
110. 3-p-isopentylthiophenyl-2-methyl-2-buten-1-amine.
111. 3-p-isopentylthiophenyl-3-phenyl-2-propen-1-amine.
112. 3-p-isopentylthiophenyl-2-methyl-3-phenyl-2-propen-1-amine.
113. 3-p-cyclohexylthiophenyl-2-propen-1-amine.
114. 3-p-cyclohexylthiophenyl-2-buten-1-amine.
115. 3-p-cyclohexylthiophenyl-2-methyl-2-propen-1-amine.
116. 3-p-cyclohexylthiophenyl-2-methyl-2-buten-1-amine.
117. 3-p-cyclohexylthiophenyl-3-phenyl-2-propen-1-amine.
118. 3-p-cyclohexylthiophenyl-2-methyl-3-phenyl-2-propen-1-amine.
119. 3-(2-dibenzothienyl)-2-propen-1-amine.
120. 3-(2-dibenzothienyl)-2-buten-1-amine.
121. 3-(2-dibenzothienyl)-2-methyl-2-propen-1-amine.
122. 3-(2-dibenzothienyl)-2-methyl-2-buten-1-amine.
123. 3-(2-dibenzothienyl)-3-phenyl-2-propen-1-amine.
124. 3-(2-dibenzothienyl)-2-methyl-3-phenyl-2-propen-1-amine
125. 1-ethylamino-3-p-isopentylthiophenyl-2-propene.

EXAMPLE 126

While stirring, a solution of 26.9 g of 3-(2-dibenzothienyl)-butyramide [obtainable from dibenzothiophene via 2-acetyl-dibenzothiophene, 3-(2-dibenzothienyl)-3-hydroxybutyric acid ethyl ester and 3-(2-dibenzothienyl)butyric acid] in 300 ml of THF is dropped into a solution of 4.6 g of diborane in 50 ml of THF. This is boiled for 2 hours, cooled and mixed with 25% hydrochloric acid. It is then poured into water and worked up with aqueous sodium hydroxide solution and ethyl acetate to obtain 3-(2-dibenzothienyl)-butyl-amine.

EXAMPLE 127

There is added 4.15 g of NaBH$_4$ portionwise to a solution of 30.8 g of 3-(1-imidazolyl)-p-phenylthiopropiophenone [m.p. 100°-102°; obtainable by Friedel-Crafts acylation of diphenyl sulphide with 3-chloropropionyl chloride and reaction of the 3-chloro-p-phenylthiopropiophenone obtained (m.p. 60°-68°) with imidazole] in 160 ml of methanol and 160 ml of THF, with stirring. This is further stirred for 1 hour at 20°, diluted with ice water and worked up as usual to obtain 1-(1-imidazolyl)-3-p-phenylthiophenyl-propan-3-ol; m.p. 96°-98°.

EXAMPLES 128 to 303

Analogously to Example 127, by reduction of the corresponding ketones with NaBH$_4$, there is obtained:
128. 1-methylamino-3-p-phenylthiophenyl-propan-3-ol.
129. 1-methylamino-3-p-phenylthiophenyl-propan-2-ol.
130. 1-methylamino-3-p-phenylthiophenyl-buten-2-ol.
131. 1-methylamino-3-p-phenylthiophenyl-2-methyl-propan-3-ol 132. 1-methylamino-3-p-phenylthiophenyl-3-phenyl-propan-2-ol
133. 1-methylamino-3-p-(2,4-dichlorobenzylthio)-phenyl-propan-3-ol.
134. 1-methylamino-3-p-(2,4-dichlorobenzylthio)-phenyl-propan-2-ol.
135. 1-methylamino-3-p-(2,4-dichlorobenzylthio)-phenyl-butan-2-ol.
136. 1-methylamino-3-p-(2,4-dichlorobenzylthio)-phenyl-2-methyl-propan-3-ol.
137. 1-methylamino-3-p-(2,4-dichlorobenzylthio)-phenyl-3-phenyl-propan-2-ol.
138. 1-methylamino-3-p-isopentylthiophenyl-propan-3-ol.
139. 1-methylamino-3-p-isopentylthiophenyl-propan-2-ol.
140. 1-methylamino-3-p-isopentylthiophenyl-butan-2-ol.
141. 1-methylamino-3-p-isopentylthiophenyl-2-methyl-propan-3-ol.
142. 1-methylamino-3-p-isopentylthiophenyl-3-phenyl-propan-2-ol.
143. 1-methylamino-3-p-cyclohexylthiophenyl-propan-3-ol.
144. 1-methylamino-3-p-cyclohexylthiophenyl-propan-2-ol.
145. 1-methylamino-3-p-cyclohexylthiophenyl-butan-2-ol.
146. 1-methylamino-3-p-cyclohexylthiophenyl-2-methyl-propan-3-ol.
147. 1-methylamino-3-p-cyclohexylthiophenyl-3-phenyl-propan-2-ol.
148. 1-methylamino-3-(2-dibenzothienyl)-propan-3-ol.
149. 1-methylamino-3-(2-dibenzothienyl)-propan-2-ol.
150. 1-methylamino-3-(2-dibenzothienyl)-butan-2-ol.
151. 1-methylamino-3-(2-dibenzothienyl)-2-methyl-propan-3-ol
152. 1-methylamino-3-(2-dibenzothienyl)-3-phenyl-propan-2-ol
153. 1-ethylamino-3-p-phenylthiophenyl-propan-3-ol.
154. 1-ethylamino-3-p-phenylthiophenyl-propan-2-ol.
155. 1-ethylamino-3-p-phenylthiophenyl-butan-2-ol.
156. 1-ethylamino-3-p-phenylthiophenyl-2-methyl-propan-3-ol.
157. 1-ethylamino-3-p-phenylthiophenyl-3-phenyl-propan-2-ol.
158. 1-ethylamino-3-p-(2,4-dichlorobenzylthio)-phenyl-propan-3-ol.
159. 1-ethylamino-3-p-(2,4-dichlorobenzylthio)-phenyl-propan-2-ol.
160. 1-ethylamino-3-p-(2,4-dichlorobenzylthio)-phenyl-butan-2-ol.
161. 1-ethylamino-3-p-(2,4-dichlorobenzylthio)-phenyl-2-methyl-propan-3-ol.
162. 1-ethylamino-3-p-(2,4-dichlorobenzylthio)-phenyl-3-phenyl-propan-2-ol.
163. 1-ethylamino-3-p-isopentylthiophenyl-propan-3-ol.
164. 1-ethylamino-3-p-isopentylthiophenyl-propan-2-ol.
165. 1-ethylamino-3-p-isopentylthiophenyl-butan-2-ol.
166. 1-ethylamino-3-p-isopentylthiophenyl-2-methyl-propan-3-ol.
167. 1-ethylamino-3-p-isopentylthiophenyl-3-phenyl-propan-2-ol.
168. 1-ethylamino-3-p-cyclohexylthiophenyl-propan-3-ol.
169. 1-ethylamino-3-p-cyclohexylthiophenyl-propan-2-ol.
170. 1-ethylamino-3-p-cyclohexylthiophenyl-butan-2-ol.
171. 1-ethylamino-3-p-cyclohexylthiophenyl-2-methyl-propan-3-ol.
172. 1-ethylamino-3-p-cyclohexylthiophenyl-3-phenyl-propan-2-ol.
173. 1-ethylamino-3-(2-dibenzothienyl)-propan-3-ol.
174. 1-ethylamino-3-(2-dibenzothienyl)-propan-2-ol.
175. 1-ethylamino-3-(2-dibenzothienyl)-butan-2-ol.
176. 1-ethylamino-3-(2-dibenzothienyl)-2-methyl-propan-3-ol.
177. 1-ethylamino-3-(2-dibenzothienyl)-3-phenyl-propan-2-ol.
178. 1-dimethylamino-3-p-phenylthiophenyl-propan-3-ol.
179. 1-dimethylamino-3-p-phenylthiophenyl-propan-2-ol.
180. 1-dimethylamino-3-p-phenylthiophenyl-butan-2-ol.
181. 1-dimethylamino-3-p-phenylthiophenyl-2-methyl-propan-3-ol; m.p. 73°–74°.
182. 1-dimethylamino-3-p-phenylthiophenyl-3-phenyl-propan-2-ol.
183. 1-dimethylamino-4-p-phenylthiophenyl-butan-4-ol.
184. 1-dimethylamino-5-p-phenylthiophenyl-pentan-5-ol.
185. 1-dimethylamino-3-p-(p-fluorophenylthio)-phenyl-propan-3-ol.
186. 1-dimethylamino-3-p-(o-chlorophenylthio)-phenyl-propan-3-ol.
187. 1-dimethylamino-3-p-(p-chlorophenylthio)-phenyl-propan-3-ol.
188. 1-dimethylamino-3-p-(2,4-dichlorophenylthio)-phenyl-propan-3-ol.
189. 1-dimethylamino-3-p-(p-bromophenylthio)-phenyl-propan-3-ol.
190. 1-dimethylamino-3-p-(p-iodophenylthio)-phenyl-propan-3-ol.
191. 1-dimethylamino-3-p-(p-nitrophenylthio)-phenyl-propan-3-ol.
192. 1-dimethylamino-3-p-(p-aminophenylthio)-phenyl-propan-3-ol.
193. 1-dimethylamino-3-p-(p-methoxyphenylthio)-phenyl-propan-3-ol.
194. 1-dimethylamino-3-p-(p-n-butoxyphenylthio)-phenyl-propan-3-ol.
195. 1-dimethylamino-3-p-benzylthiophenyl-propan-3ol.
196. 1-dimethylamino-3-p-(p-chlorobenzylthio)-phenyl-propan-3-ol.
197. 1-dimethylamino-3-p-(2,4-dichlorobenzylthio)-phenyl-propan-3-ol; m.p. 99°–101°.
198. 1-dimethylamino-3-p-(2,4-dichlorobenzylthio)-phenyl-propan-2-ol.
199. 1-dimethylamino-3-p-(2,4-dichlorobenzylthio)-phenyl-butan-2-ol.
200. 1-dimethylamino-3-p-(2,4-dichlorobenzylthio)-phenyl-2-methyl-propan-3-ol.
201. 1-dimethylamino-3-p-(2,4-dichlorobenzylthio)-phenyl-3-phenyl-propan-2-ol.
202. 1-dimethylamino-3-p-methylthiophenyl-propan-3-ol.
203. 1-dimethylamino-3-p-ethylthiophenyl-propan-3-ol.
204. 1-dimethylamino-3-p-isopropylthiophenyl-propan-3-ol.
205. 1-dimethylamino-3-p-isobutylthiophenyl-propan-3-ol.
206. 1-dimethylamino-3-p-isopentylthiophenyl-propan-3-ol.

207. 1-dimethylamino-3-p-isopentylthiophenyl-propan-2-ol.
208. 1-dimethylamino-3-p-isopentylthiophenyl-butan-2-ol.
209. 1-dimethylamino-3-isopentylthiophenyl-2-methyl-propan-3-ol.
210. 1-dimethylamino-3-p-isopentylthiophenyl-3-phenyl-propan-2-ol.
211. 1-dimethylamino-3-p-isopentylthiophenyl-2-n-butyl-propan-3-ol, $n_D^{20}$ 1.5267 (by reaction of 1-p-isopentylthiophenyl-hexan-1-one (b.p. 183°–186°/0.15 mm.) with $(CH_3)_2NH/HCHO$ to give 1-dimethylamino-3-p-isopentylthiophenyl-2-n-butyl-propan-3-one and reduction).
212. 1-dimethylamino-3-p-isohexylthiophenyl-propan-3-ol.
213. 1-dimethylamino-3-p-cyclopropylthiophenyl-propan-3-ol.
214. 1-dimethylamino-3-p-cyclopentylthiophenyl-propan-3-ol.
215. 1-dimethylamino-3-p-cyclohexylthiophenyl-propan-3-ol.
216. 1-dimethylamino-3-p-cyclohexylthiophenyl-propan-2-ol.
217. 1-dimethylamino-3-p-cyclohexylthiophenyl-butan-2-ol.
218. 1-dimethylamino-3-p-cyclohexylthiophenyl-2-methyl-propan-3-ol.
219. 1-dimethylamino-3-p-cyclohexylthiophenyl-3-phenyl-propan-2-ol.
220. 1-dimethylamino-3-p-cycloheptylthiophenyl-propan-3-ol.
221. 1-dimethylamino-3-(2-dibenzothienyl)-propan-3-ol; m.p. 119°–120°.
222. 1-dimethylamino-3-(2-dibenzothienyl)-propan-2-ol.
223. 1-dimethylamino-3-(2-dibenzothienyl)-butan-2-ol.
224. 1-dimethylamino-3-(2-dibenzothienyl)-2-methyl-propan-3-ol.
225. 1-dimethylamino-3-(2-dibenzothienyl)-3-phenyl-propan-2-ol.
226. 1-diethylamino-3-p-phenylthiophenyl-propan-3-ol.
227. 1-diethylamino-3-p-phenylthiophenyl-propan-2-ol.
228. 1-diethylamino-3-p-phenylthiophenyl-butan-3-ol.
229. 1-diethylamino-3-p-phenylthio-phenyl-2-methyl-propan-3-ol.
230. 1-diethylamino-3-p-phenylthio-phenyl-3-phenyl-propan-2-ol.
231. 1-diethylamino-3-p-(2,4-dichlorobenzylthio)-phenyl-propan-3-ol.
232. 1-diethylamino-3-p-(2,4-dichlorobenzylthio)-phenyl-propan-2-ol.
233. 1-diethylamino-3-p-(2,4-dichlorobenzylthio)-phenyl-butan-2-ol.
234. 1-diethylamino-3-p-(2,4-dichlorobenzylthio)-phenyl-2-methyl-propan-3-ol.
235. 1-diethylamino-3-p-(2,4-dichlorobenzylthio)-phenyl-3-phenyl-propan-2-ol.
236. 1-diethylamino-3-p-isopentylthiophenyl-propan-3-ol.
237. 1-diethylamino-3-p-isopentylthiophenyl-propan-2-ol.
238. 1-diethylamino-3-p-isopentylthiophenyl-butan-2-ol.
239. 1-diethylamino-3-p-isopentylthiophenyl-2-methyl-propan-3-ol.
240. 1-diethylamino-3-p-isopentylthiophenyl-3-phenyl-propan-2-ol.
241. 1-diethylamino-3-p-cyclohexylthiophenyl-propan-3-ol.
242. 1-diethylamino-3-p-cyclohexylthiophenyl-propan-2-ol.
243. 1-diethylamino-3-p-cyclohexylthiophenyl-butan-2-ol.
244. 1-diethylamino-3-p-cyclohexylthiophenyl-2-methyl-propan-3-ol.
245. 1-diethylamino-3-p-cyclohexylthiophenyl-3-phenyl-propan-2-ol.
246. 1-diethylamino-3-(2-dibenzothienyl)-propan-3-ol.
247. 1-diethylamino-3-(2-dibenzothienyl)-propan-2-ol.
248. 1-diethylamino-3-(2-dibenzothienyl)-butan-2-ol.
249. 1-diethylamino-3-(2-dibenzothienyl)-2-methyl-propan-3-ol.
250. 1-diethylamino-3-(2-dibenzotheinyl)-3-phenyl-propan-2-ol.
251. 1-di-n-butylamino-3-p-isopentylthiophenyl-propan-3-ol.
252. 1-pyrrolidino-3-p-isopentylthiophenyl-propan-3-ol.
253. 1-piperidino-3-p-isopentylthiophenyl-propan-3-ol.
254. 1-(4-methylpiperidino)-3-p-methylthiophenyl-propan-3-ol, hydrochloride, m.p. 121°–123°.
255. 1-(4-methylpiperidino)-3-p-isopentylthiophenyl-propan-3-ol.
256. 1-morpholino-3-p-isopentylthiophenyl-propan-3-ol.
257. 1-(1-imidazolyl)-3-p-phenylthiophenyl-propan-2-ol.
258. 1-(1-imidazolyl)-3-p-phenylthiophenyl-butan-2-ol.
259. 1-(1-imidazolyl)-3-p-phenylthiophenyl-2-methyl-propan-3-ol, m.p. 128°–132°.
260. 1-(1-imidazolyl)-3-p-phenylthiophenyl-3-phenyl-propan-2-ol.
261. 1-(1-imidazolyl)-4-p-phenylthiophenyl-butan-4-ol.
262. 1-(1-imidazolyl)-5-p-phenylthiophenyl-pentan-5-ol.
263. 1-(1-imidazolyl)-3-p-(p-fluorophenylthio)-phenyl-propan-3-ol.
264. 1-(1-imidazolyl)-3-p-(o-chlorophenylthio)-phenyl-propan-3-ol.
265. 1-(1-imidazolyl)-3-p-(p-chlorophenylthio)-phenyl-propan-3-ol.
266. 1-(1-imidazolyl)-3-p-(2,4-dichlorophenylthio)-phenyl-propan-3-ol.
267. 1-(1-imidazolyl)-3-p-(p-bromophenylthio)-phenyl-propan-3-ol, m.p. 93°–96°.
268. 1-(1-imidazolyl)-3-p-(p-iodophenylthio)-phenyl-propan-3-ol.
269. 1-(1-imidazolyl)-3-p-(p-nitrophenylthio)-phenyl-propan-3-ol, m.p. 155°–158°.
270. 1-(1-imidazolyl)-3-p-(p-aminophenylthio)-phenyl-propan-3-ol, m.p. 133°–135°.
271. 1-(1-imidazolyl)-3-p-(p-methoxyphenylthio)-phenyl-propan-3-ol, m.p. 83°–84°.
272. 1-(1-imidazolyl)-3-p-(p-n-butoxyphenylthio)-phenyl-propan-3-ol.
273. 1-(1-imidazolyl)-3-p-benzylthiophenyl-propan-3-ol.
274. 1-(1-imidazolyl)-3-p-(p-chlorobenzylthio)-phenyl-propan-3-ol.
275. 1-(1-imidazolyl)-3-p-(2,4-dichlorobenzylthio)-phenyl-propan-3-ol, m.p. 133°–136°.
276. 1-(1-imidazolyl)-3-p-(2,4-dichlorobenzylthio)-phenyl-propan-2-ol.
277. 1-(1-imidazolyl)-3-p-(2,4-dichlorobenzylthio)-phenyl-butan-2-ol.
278. 1-(1-imidazolyl)-3-p-(2,4-dichlorobenzylthio)-phenyl-2-methyl-propan-3-ol.

279. 1-(1-imidazolyl)-3-p-(2,4-dichlorobenzylthio)-phenyl-3-phenyl-propan-2-ol.
280. 1-(1midazol-1-yl)-3-p-methylthiophenyl-propan-3-ol.
281. 1-(imidazol-1-yl)-3-p-ethylthiophenyl-propan-3-ol.
282. 1-(imidazol-1-yl)-3-p-isopropylthiophenyl-propan-3-ol.
283. 1-(imidazol-1-yl)-3-p-isobutylthiophenyl-propan-3-ol.
284. 1-(imidazol-1-yl)-3-p-isopentylthiophenyl-propan-3-ol, m.p. 89°–90°.
285. 1-(imidazol-1-yl)-3-isopentylthiophenyl-propan-2-ol.
286. 1-(imidazol-1-yl)-3-p-isopentylthiophenyl-butan-2-ol.
287. 1-(imidazol-1-yl)-3-p-isopentylthiophenyl-2-methyl-propan-3-ol.
288. 1-(imidazol-1-yl)-3-p-isopentylthiophenyl-3-phenyl-propan-2-ol.
289. 1-(imidazol-1-yl)-3-p-isohexylthiophenyl-propan-3-ol.
290. 1-(imidazol-1-yl)-3-p-cyclopropylthiophenyl-propan-3-ol.
291. 1-(imidazol-1-yl)-3-p-cyclopentylthiophenyl-propan-3-ol.
292. 1-(imidazol-1-yl)-3-p-cyclohexylthiophenyl-propan-3-ol.
293. 1-(imidazol-1-yl)-3-p-cyclohexylthiophenyl-propan-2-ol.
294. 1-(imidazol-1-yl)-3-p-cyclohexylthiophenyl-butan-2-ol.
295. 1-(imidazol-1-yl)-3-p-cyclohexylthiophenyl-2-methyl-propan-3-ol.
296. 1-(imidazol-1-yl)-3-p-cyclohexylthiophenyl-3-phenyl-propan-2-ol.
297. 1-(imidazol-1-yl)-3-p-cycloheptylthiophenyl-propan-3-ol.
298. 1-(imidazol-1-yl)-3-(2-dibenzothienyl)-propan-3-ol.
299. 1-(imidazol-1-yl)-3-(2-dibenzothienyl)-propan-2-ol.
300. 1-(imidazol-1-yl)-3-(2-dibenzothienyl)-butan-2-ol.
301. 1-(imidazol-1-yl)-3-(2-dibenzothienyl)-2-methyl-propan-3-ol.
302. 1-(imidazol-1-yl)-3-(2-dibenzothienyl)-3-phenyl-propan-2-ol.
303. 1-(1,2,4-triazol-1-yl)-3-p-isopentylthiophenyl-propan-3-ol.

EXAMPLE 304

A solution of 23.7 g of 3-(2-dibenzothienyl)propionitrile (obtainable from the amide with p-toluenesulphonyl chloride/pyridine) in 250 ml of methanol, is hydrogenated with the addition of 8 g of KOH and 12 g of Raney nickel, at about 80 atm. and 80° for 3 hours. This is filtered, evaporated and worked up with water and dichloromethane. After drying and evaporating of the organic phase, there is obtained 3-(2-dibenzothienyl)-propylamine.

EXAMPLE 305

A solution of 26.7 g of 1-nitro-3-p-isopentylthiophenylpropane [obtainable by reduction of 3-p-isopentyl-thiophenylpropionic acid with LiAlH$_4$ to the alcohol, reaction with PBr$_3$ to 1-bromo-3-p-isopentylthiophenyl-propane and reaction with NaNO$_2$] in 500 ml of hot ethanol is mixed with a solution of 80 g of Na$_2$S$_2$O$_4$ in 350 ml of water. The mixture is boiled for one hour, concentrated and worked up with aqueous sodium hydroxide solution and chloroform to obtain 3-p-isopentylthiophenyl-propylamine. Hydrochloride, m.p. 193° (decomposition).

EXAMPLE 306

A mixture of 24 g of 3-(2-dibenzothienyl)-propanal (obtainable by the Rosenmundreaction from the acid), 40 g of liquid ammonia and 400 ml of methanol is heated for twelve hours at 100°. 1-Hydroxy-3-(2-dibenzothienyl)-propylamine and 3-(2-dibenzothienyl)-propylidene-imine, thereby presumably formed as intermediate products, are not isolated. 30 g of Raney nickel is added. The mixture is hydrogenated for about 20 hours at 100 atm. and 100°, filtered and evaporated to obtain 3-(2-dibenzothienyl)-propylamine.

EXAMPLE 307

25.5 g of 3-(2-dibenzothienyl)-propanaldoxime (obtainable from the aldehyde and hydroxylamine) is dissolved in 500 ml of ethanol. This is hydrogenated on 3 g of PtO$_2$ at 20° and normal pressure up to cessation, filtered and evaporated to obtain 3-(2-dibenzothienyl)-propylamine.

EXAMPLE 308

23.5 g of 3-(2-dibenzothienyl)-propenic acid nitrile (obtainable from 3-formyl-dibenzothiophene and cyanoacetic acid) is dissolved in 150 ml of isopropanol. 15 g of liquid NH$_3$ and 3 g of isopropanol-moist Raney Ni are added. This is hydrogenated at 80° and 80 atm. for 4 hours. After filtering and evaporating, there is obtained 3-(2-dibenzothienyl)-propylamine.

EXAMPLE 309

A solution of 33.1 g of N-benzyl-3-(2-dibenzothienyl)propylamine [obtainable by reaction of 3-(2-dibenzothienyl)propanol with SOCl$_2$ to give 1-chloro-3-(2-dibenzothienyl)propane and reaction with benzylamine] in 500 ml of methanol is hydrogenated on 8 g of 5% Pd-charcoal at 20° and normal pressure. After filtering and evaporating, there is obtained 3-(2-dibenzothienyl)-propylamine.

The same product is obtainable analogously from N-benzylidene-3-(2-dibenzothienyl)-propylamine or from N,N-dibenzyl-3-(2-dibenzothienyl)-propylamine.

EXAMPLE 310

A solution of 2.95 g of 1-isobutylideneamino-3-(2-dibenzothienyl)-propane (obtainable by 5 hours boiling of 3-(2-dibenzothienyl)-propylamine with isobutyraldehyde in benzene) in 75 ml of methanol is, after the addition of 0.3 g of PtO$_2$, hydrogenated at 20° and normal pressure up to the end of the take up of hydrogen. This is filtered and worked up as usual to obtain 1-isobutylamino-3-(2-dibenzothienyl)-propane.

EXAMPLE 311

A solution of 2.81 g of 1-isopropylimino-3-(2-dibenzothienyl)-propane (obtainable from 3-(2-dibenzothienyl)-propanal and isopropylamine) in 25 ml of dioxane is hydrogenated on 0.2 g of platinum at 20° and normal pressure up to the end of the take up of hydrogen. This is filtered and evaporated to obtain 1-isopropylamino-3-(2-dibenzothienyl)-propane.

EXAMPLE 312

A solution of 2.38 g of 3-(2-dibenzothienyl)-propenal (obtainable by reaction of 2-formyl-dibenzothiophene with 2,2-diethoxyethyl magnesium bromide and subsequent dehydration with p-toluene-sulphonic acid) and 0.6 g of isopropylamine in 25 ml of methanol is heated in a tube for 5 hours at 200°. After cooling, 0.5 g of methanol-moist Raney nickel is added. The Schiff base obtained is hydrogenated at 100 atm. and 80° for one hour. This is cooled and filtered to obtain 1-isopropylamino-3-(2-dibenzothienyl)-propane.

EXAMPLE 313

A solution of 2.75 g of 1-isopropylimino-3-p-isopentylthiophenyl-2-propene (obtainable from p-isopentylthiocinnamic aldehyde and isopropylamine) in 20 ml of absolute ether is added dropwise to a solution of 0.6 g of LiAlH$_4$ in 20 ml of absolute ether. Subsequently, the mixture is boiled for 5 hours, carefully mixed with water and worked up as usual to obtain 1-isopropylamino-3-p-isopentylthiophenyl-2-propene.

EXAMPLE 314

A solution of 2.93 g of 1-pyrrolidino-3-(2-dibenzothienyl)-1-propene [obtainable from 3-(2-dibenzothienyl)-propanal and pyrrolidine] in 35 ml of ethanol is hydrogenated on 0.5 g of Raney nickel at 6 atm. and 60° for 3 hours. The catalyst is filtered off and the solution is evaporated to obtain 1-pyrrolidino-3-(2-dibenzothienyl)-propane.

EXAMPLE 315

A solution of 2.57 g of 3-p-phenylthiophenyl-propanaldoxime in 25 ml of acetic acid is mixed, while stirring, with 1.5 g of zinc dust. This is stirred for a further 4 hours, diluted with water, made alkaline with ammonia and extracted with chloroform. After the usual working up, 3-p-phenylthiophenyl-propylamine is obtained.

EXAMPLE 316

Analogously to Example 1, from 1-(2-oxo-piperidino)-3-p-isopentylthiophenyl-propane (obtainable from 3-p-isopentylthiophenyl-propylamine and 5-bromo-valeryl bromide) and LiAlH$_4$,1-piperidino-3-p-isopentylthiophenyl-propane is obtained.

EXAMPLE 317

A mixture of 3.19 g of 1-(4-oxo-piperidino)-3-p-isopentylthiophenyl-propane (obtainable from 1-chloro-3-p-isopentylthiophenyl-propane and 4-piperidone), 1.5 g of KOH, 2.5 ml of 85% hydrazine and 25 ml of diethylene glycol is heated for 1 hour at 100°. The temperature is slowly increased up to the decomposition of the hydrazone, further boiled for 4 hours, cooled and worked up as usual to obtain 1-piperidino-3-p-isopentylthiophenyl-propane.

EXAMPLE 318

4.21 g of 1-dibenzylamino-3-(2-dibenzothienyl)-propane [obtainable by reaction of 1-chloro-3-(2-dibenzothienyl)-propane with dibenzylamine] is dissolved in 50 ml of ethyl acetate. This is hydrogenated on 0.5 g of 10% Pd-C at 20° and 1 atm. up to the point of cessation. This is filtered and evaporated to obtain 3-(2-dibenzothienyl)-propylamine.

EXAMPLE 319

A solution of 25.1 g of 1-amino-3-p-isopentylthiophenylpropan-3 -one (obtainable by reaction of 1-chloro-3-p-isopentylthiophenyl-propan-3-one with potassium phthalimide and subsequent hydrolysis) in 200 ml of THF is added dropwise, with stirring at 20°, to a Grignard solution in 1000 ml of ether prepared from 30 g of CH$_3$I and 5 g of magnesium. This is further stirred for 4 hours, decomposed with water and dilute sulphuric acid the alcoholate obtained, of the formula p—(CH$_3$)$_2$CH(CH$_2$)$_2$S—C$_6$H$_4$—C(CH$_3$)(OMgI)—CH$_2$CH$_2$NH$_2$, is worked up as usual to obtain 3-p-isopentylthiophenyl-3-hydroxybutylamine.

EXAMPLE 320

190 ml of a 1.6 molar CH$_3$Li solution in ether is added dropwise under N$_2$ and stirring, to a boiling solution of 29.1 g of 3-dimethylamino-p-cyclohexylthiopropiophenone (obtainable by acylation of phenyl-chclohexyl-sulphide with 3-chloropropionyl chloride and subsequent reaction with dimethylamine) in 350 ml of ether. This is further stirred for one hour at 25° and for 2.5 hours at 35°. The lithium 1-dimethylamino-3-p-cyclohexylthiophenyl-butan-3-olate obtained is decomposed by the addition of 200 ml of saturated NH$_4$Cl solution, with ice cooling. After the usual working up, 1-dimethylamino-3-p-cyclohexylthiophenyl-butan-3-ol, oil is obtained.

EXAMPLES 321 to 498

Analogously to Example 320, there is obtained by reaction of the corresponding ketones with CH$_3$Li or C$_6$H$_5$Li and subsequent hydrolysis:

321. 1-methylamino-3-p-phenylthiophenyl-butan-3-ol.
322. 1-methylamino-3-p-phenylthiophenyl-2-methyl-propan-2-ol.
323. 1-methylamino-3-p-phenylthiophenyl-2-methyl-butan-3-ol.
324. 1-methylamino-3-p-phenylthiophenyl-2-methyl-butan-2-ol.
325. 1-methylamino-3-p-phenylthiophenyl-3-phenyl-propan-3-ol.
326. 1-methylamino-3-p-phenylthiophenyl-2-methyl-3-phenyl-propan-3-ol.
327. 1-methylamino-3-p-phenylthiophenyl-2-methyl-3-phenyl-propan-2-ol.
328. 1-methylamino-3-p-(2,4-dichlorobenzylthio)-phenyl-butan-3-ol.
329. 1-methylamino-3-p-(2,4-dichlorobenzylthio)-phenyl-2-methyl-propan-2-ol.
330. 1-methylamino-3-p-(2,4-dichlorobenzylthio)-phenyl-2-methyl-butan-3-ol.
331. 1-methylamino-3-p-(2,4-dichlorobenzylthio)-phenyl-2-methyl-butan-2-ol.
332. 1-methylamino-3-p-(2,4-dichlorobenzylthio)-phenyl-3-phenyl-propan-3-ol.
333. 1-methylamino-3-p-(2,4-dichlorobenzylthio)-phenyl-2-methyl-3-phenyl-propan-3-ol.
334. 1-methylamino-3-p-(2,4-dichlorobenzylthio)-phenyl-2-methyl-3-phenyl-propan-2-ol.
335. 1-methylamino-3-p-isopentylthiophenyl-butan-3-ol.
336. 1-methylamino-3-p-isopentylthiophenyl-2-methyl-propan-2-ol.
337. 1-methylamino-3-p-isopentylthiophenyl-2-methyl-butan-3-ol.
338. 1-methylamino-3-p-isopentylthiophenyl-2-methyl-butan-2-ol.
339. 1-methylamino-3-p-isopentylthiophenyl-3-phenyl-propan-3-ol.
340. 1-methylamino-3-p-isopentylthiophenyl-2-methyl-3-phenyl-propan-3-ol.
341. 1-methylamino-3-p-isopentylthiophenyl-2-methyl-3-phenyl-propan-2-ol.

342. 1-methylamino-3-p-cyclohexylthiophenyl-butan-3-ol.
343. 1-methylamino-3-p-cyclohexylthiophenyl-2-methyl-propan-2-ol.
344. 1-methylamino-3-p-cyclohexylthiophenyl-2-methyl-butan-3-ol.
345. 1-methylamino-3-p-cyclohexylthiophenyl-2-methyl-butan-2-ol.
346. 1-methylamino-3-p-cyclohexylthiophenyl-3-phenyl-propan-3-ol.
347. 1-methylamino-3-p-cyclohexylthiophenyl-2-methyl-3-phenyl-propan-3-ol.
348. 1-methylamino-3-p-cyclohexylthiophenyl-2-methyl-3-phenyl-propan-2-ol.
349. 1-methylamino-3-(2-dibenzothienyl)-butan-3-ol.
350. 1-methylamino-3-(2-dibenzothienyl)-2-methyl-propan-2-ol.
351. 1-methylamino-3-(2-dibenzothienyl)-2-methyl-butan-3-ol.
352. 1-methylamino-3-(2-dibenzothienyl)-2-methyl-butan-2-ol.
353. 1-methylamino-3-(2-dibenzothienyl)-3-phenyl-propan-3-ol.
354. 1-methylamino-3-(2-dibenzothienyl)-2-methyl-3-phenyl-propan-3-ol.
355. 1-methylamino-3-(2-dibenzothienyl)-2-methyl-3-phenyl-propan-2-ol.
356. 1-ethylamino-3-p-phenylthiophenyl-butan-3-ol.
357. 1-ethylamino-3-p-phenylthiophenyl-2-methyl-propan-2-ol.
358. 1-ethylamino-3-p-phenylthiophenyl-2-methyl-butan-3-ol.
359. 1-ethylamino-3-p-phenylthiophenyl-2-methyl-butan-2-ol.
360. 1-ethylamino-3-p-phenylthiophenyl-3-phenyl-propan-3-ol.
361. 1-ethylamino-3-p-phenylthiophenyl-2-methyl-3-phenyl-propan-3-ol.
362. 1-ethylamino-3-p-phenylthiophenyl-2-methyl-3-phenyl-propan-2-ol.
363. 1-ethylamino-3-p-(2,4-dichlorobenzylthio)-phenyl-butan-3-ol.
364. 1-ethylamino-3-p-(2,4-dichlorobenzylthio)-phenyl-2-methyl-propan-2-ol.
365. 1-ethylamino-3-p-(2,4-dichlorobenzylthio)-phenyl-2-methyl-butan-3-ol.
366. 1-ethylamino-3-p-(2,4-dichlorobenzylthio)-phenyl-2-methyl-butan-2-ol.
367. 1-ethylamino-3-p-(2,4-dichlorobenzylthio)-phenyl-3-phenyl-propan-3-ol.
368. 1-ethylamino-3-p-(2,4-dichlorobenzylthio)-phenyl-2-methyl-3-phenyl-propan-3-ol.
369. 1-ethylamino-3-p-(2,4-dichlorobenzylthio)-phenyl-2-methyl-3-phenyl-propan-2-ol.
370. 1-ethylamino-3-p-isopentylthiophenyl-butan-3-ol.
371. 1-ethylamino-3-p-isopentylthiophenyl-2-methyl-propan-2-ol.
372. 1-ethylamino-3-p-isopentylthiophenyl-2-methyl-butan-3-ol.
373. 1-ethylamino-3-p-isopentylthiophenyl-2-methyl-butan-2-ol.
374. 1-ethylamino-3-p-isopentylthiophenyl-3-phenyl-propane-3-ol.
375. 1-ethylamino-3-p-isopentylthiophenyl-2-methyl-3-phenyl-propan-3-ol.
376. 1-ethylamino-3-p-isopentylthiophenyl-2-methyl-3-phenyl-propan-2-ol.
377. 1-ethylamino-3-p-cyclohexylthiophenyl-butan-3-ol.
378. 1-ethylamino-3-p-cyclohexylthiophenyl-2-methyl-propan-2-ol.
379. 1-ethylamino-3-p-cyclohexylthiophenyl-2-methyl-butan-3-ol.
380. 1-ethylamino-3-p-cyclohexylthiophenyl-2-methyl-butan-2-ol.
381. 1-ethylamino-3-p-cyclohexylthiophenyl-3-phenyl-propan-3-ol.
382. 1-ethylamino-3-p-cyclohexylthiophenyl-2-methyl-3-phenyl-propan-3-ol.
383. 1-ethylamino-3-p-cyclohexylthiophenyl-2-methyl-3-phenyl-propan-2-ol.
384. 1-ethylamino-3-(2-dibenzothienyl)-butan-3-ol.
385. 1-ethylamino-3-(2-dibenzothienyl)-2-methyl-propan-2-ol.
386. 1-ethylamino-3-(2-dibenzothienyl)-2-methyl-butan-3-ol.
387. 1-ethylamino-3-(2-dibenzothienyl)-2-methyl-butan-2-ol.
388. 1-ethylamino-3-(2-dibenzothienyl)-3-phenyl-propan-3-ol.
389. 1-ethylamino-3-(2-dibenzothienyl)-2-methyl-3-phenyl-propan-3-ol.
390. 1-ethylamino-3-(2-dibenzothienyl)-2-methyl-3-phenyl-propan-2-ol.
391. 1-dimethylamino-3-p-phenylthiophenyl-butan-3-ol.
392. 1-dimethylamino-3-p-phenylthiophenyl-2-methyl-propan-2-ol.
393. 1-dimethylamino-3-p-phenylthiophenyl-2-methyl-butan-3-ol.
394. 1-dimethylamino-3-p-phenylthiophenyl-2-methyl-butan-2-ol.
395. 1-dimethylamino-3-p-phenylthiophenyl-3-phenyl-propan-3-ol.
396. 1-dimethylamino-3-p-phenylthiophenyl-2-methyl-3-phenyl-propan-3-ol.
397. 1-dimethylamino-3-p-phenylthiophenyl-2-methyl-3-phenyl-propan-2-ol.
398. 1-dimethylamino-4-p-phenylthiophenyl-pentan-4-ol.
399. 1-dimethylamino-5-p-phenylthiophenyl-hexan-5-ol.
400. 1-dimethylamino-3-p-(2,4-dichlorobenzylthio)-phenyl-butan-3-ol.
401. 1-dimethylamino-3-p-(2,4-dichlorobenzylthio)-phenyl-2-methyl-propan-2-ol.
402. 1-dimethylamino-3-p-(2,4-dichlorobenzylthio)-phenyl-2-methyl-butan-3-ol.
403. 1-dimethylamino-3-p-(2,4-dichlorobenzylthio)-phenyl-2-methyl-butan-2-ol.
404. 1-dimethylamino-3-p-(2,4-dichlorobenzylthio)-phenyl-3-phenyl-propan-3-ol.
405. 1-dimethylamino-3-p-(2,4-dichlorobenzylthio)-phenyl-2-methyl-3-phenyl-propan-3-ol.
406. 1-dimethylamino-3-p-(2,4-dichlorobenzylthio)-phenyl-2-methyl-3-phenyl-propan-2-ol.
407. 1-dimethylamino-3-isopentylthiophenyl-butan-3-ol.
408. 1-dimethylamino-3-p-isopentylthiophenyl-2-methyl-propan-2-ol.
409. 1-dimethylamino-3-p-isopentylthiophenyl-2-methyl-butan-3-ol.
410. 1-dimethylamino-3-p-isopentylthiophenyl-2-methyl-butan-2-ol.
411. 1-dimethylamino-3-p-isopentylthiophenyl-3-phenyl-propan-3-ol.

412. 1-dimethylamino-3-p-isopentylthiophenyl-2-methyl-3-phenyl-propan-3-ol.
413. 1-dimethylamino-3-p-isopentylthiophenyl-2-methyl-3-phenyl-propan-2-ol.
414. 1-dimethylamino-3-p-cyclohexylthiophenyl-2-methyl-propan-2-ol.
415. 1-dimethylamino-3-p-cyclohexylthiophenyl-2-methyl-butan-3-ol.
416. 1-dimethylamino-3-p-cyclohexylthiophenyl-2-methyl-butan-2-ol.
417. 1-dimethylamino-3-p-cyclohexylthio-phenyl-3-phenyl-propan-3-ol.
418. 1-dimethylamino-3-p-cyclohexylthiophenyl-2-methyl-3-phenyl-propan-3-ol.
419. 1-dimethylamino-3-p-cyclohexylthiophenyl-2-methyl-3-phenyl-propan-2-ol.
420. 1-dimethylamino-3-(2-dibenzothienyl)-butan-3-ol.
421. 1-dimethylamino-3-(2-dibenzothienyl)-2-methyl-propan-2-ol.
422. 1-dimethylamino-3-(2-dibenzothienyl)-2-methyl-butan-3-ol.
423. 1-dimethylamino-3-(2-dibenzothienyl)-2-methyl-butan-2-ol.
424. 1-dimethylamino-3-(2-dibenzothienyl)-3-phenyl-propan-3-ol.
425. 1-dimethylamino-3-(2-dibenzothienyl)-2-methyl-3-phenyl-propan-3-ol.
426. 1-dimethylamino-3-(2-dibenzothienyl)-2-methyl-3-phenyl-propan-2-ol.
427. 1-diethylamino-3-p-phenylthiophenyl-butan-3-ol.
428. 1-diethylamino-3-p-phenylthiophenyl-2-methyl-propan-2-ol.
429. 1-diethylamino-3-p-phenylthiophenyl-2-methyl-butan-3-ol.
430. 1-diethylamino-3-p-phenylthiophenyl-2-methyl-butan-2-ol.
431. 1-diethylamino-3-p-phenylthiophenyl-3-phenyl-propan-3-ol.
432. 1-diethylamino-3-p-phenylthiophenyl-2-methyl-3-phenyl-propan-3-ol.
433. 1-diethylamino-3-p-phenylthiophenyl-2-methyl-3-phenyl-propan-2-ol.
434. 1-diethylamino-3-p-(2,4-dichlorobenzylthio)-phenyl-butan-3-ol.
435. 1-diethylamino-3-p-(2,4-dichlorobenzylthio)-phenyl-2-methyl-propan-2-ol.
436. 1-diethylamino-3-p-(2,4-dichlorobenzylthio)-phenyl-2-methyl-butan-3-ol.
437. 1-diethylamino-3-p-(2,4-dichlorobenzylthio)-phenyl-2-methyl-butan-2-ol.
438. 1-diethylamino-3-p-(2,4-dichlorobenzylthio)-phenyl-3-phenyl-propan-3-ol.
439. 1-diethylamino-3-p-(2,4-dichlorobenzylthio)-phenyl-2-methyl-3-phenyl-propan-3-ol.
440. 1-diethylamino-3-p-(2,4-dichlorobenzylthio)-phenyl-2-methyl-3-phenyl-propan-2-ol.
441. 1-diethylamino-3-p-isopentylthiophenyl-butan-3-ol.
442. 1-diethylamino-3-p-isopentylthiophenyl-2-methyl-propan-2-ol.
443. 1-diethylamino-3-p-isopentylthiophenyl-2-methyl-butan-3-ol.
444. 1-diethylamino-3-p-isopentylthiophenyl-2-methyl-butan-2-ol.
445. 1-diethylamino-3-p-isopentylthiophenyl-3-phenyl-propan-3-ol.
446. 1-diethylamino-3-p-isopentylthiophenyl-2-methyl-3-phenyl-propan-3-ol.
447. 1-diethylamino-3-p-isopentylthiophenyl-2-methyl-3-phenyl-propan-2-ol.
448. 1-diethylamino-3-p-cyclohexylthiophenyl-butan-3-ol.
449. 1-diethylamino-3-p-cyclohexylthiophenyl-2-methyl-propan-2-ol.
450. 1-diethylamino-3-p-cyclohexylthiophenyl-2-methyl-butan-3-ol.
451. 1-diethylamino-3-p-cyclohexylthiophenyl-2-methyl-butan-2-ol.
452. 1-diethylamino-3-p-cyclohexylthiophenyl-3-phenyl-propan-3-ol.
453. 1-diethylamino-3-p-cyclohexylthiophenyl-2-methyl-3-phenyl-propan-3-ol.
454. 1-diethylamino-3-p-cyclohexylthiophenyl-2-methyl-3-phenyl-propan-2-ol.
455. 1-diethylamino-3-(2-dibenzothienyl)-butan-3-ol.
456. 1-diethylamino-3-(2-dibenzothienyl)-2-methyl-propan-2-ol.
457. 1-diethylamino-3-(2-dibenzothienyl)-2-methyl-butan-3-ol.
458. 1-diethylamino-3-(2-dibenzothienyl)-2-methyl-butan-2-ol.
459. 1-diethylamino-3-(2-dibenzothienyl)-3-phenyl-propan-3-ol.
460. 1-diethylamino-3-(2-dibenzothienyl)-2-methyl-3-phenyl-propan-3-ol.
461. 1-diethylamino-3-(2-dibenzothienyl)-2-methyl-3-phenyl-propan-2-ol.
462. 1-(1-imidazolyl)-3-p-phenylthiophenyl-butan-3-ol.
463. 1-(1-imidazolyl)-3-p-phenylthiophenyl-2-methyl-propan-2-ol.
464. 1-(1-imidazolyl)-3-p-phenylthiophenyl-2-methyl-butan-3-ol.
465. 1-(1-imidazolyl)-3-p-phenylthiophenyl-2-methyl-butan-2-ol.
466. 1-(1-imidazolyl)-3-p-phenylthiophenyl-3-phenyl-propan-3-ol.
467. 1-(1-imidazolyl)-3-p-phenylthiophenyl-2-methyl-3-phenyl-propan-3-ol.
468. 1-(1-imidazolyl)-3-p-phenylthiophenyl-2-methyl-3-phenyl-propan-2-ol.
469. 1-(1-imidazolyl)-4-p-phenylthiophenyl-pentan-4-ol.
470. 1-(1-imidazolyl)-5-p-phenylthiophenyl-hexan-5-ol.
471. 1-(1-imidazolyl)-3-p-(2,4-dichlorobenzylthio)-phenyl-butan-3-ol.
472. 1-(1-imidazolyl)-3-p-(2,4-dichlorobenzylthio)-phenyl-2-methyl-propan-2-ol.
473. 1-(1-imidazolyl)-3-p-(2,4-dichlorobenzylthio)-phenyl-2-methyl-butan-3-ol.
474. 1-(1-imidazolyl)-3-p-(2,4-dichlorobenzylthio)-phenyl-2-methyl-butan-2-ol.
475. 1-(1-imidazolyl)-3-p-(2,4-dichlorobenzylthio)-phenyl-3-phenyl-propan-3-ol.
476. 1-(1-imidazolyl)-3-p-(2,4-dichlorobenzylthio)-phenyl-2-methyl-3-phenyl-propan-3-ol.
477. 1-(1-imidazolyl)-3-p-(2,4-dichlorobenzylthio)-phenyl-2-methyl-3-phenyl-propan-2-ol.
478. 1-(1-imidazolyl)-3-p-isopentylthiophenyl-butan-3-ol.
479. 1-(1-imidazolyl)-3-p-isopentylthiophenyl-2-methyl-propan-2-ol.
480. 1-(1-imidazolyl)-3-p-isopentylthiophenyl-2-methyl-butan-3-ol.
481. 1-(1-imidazolyl)-3-p-isopentylthiophenyl-2-methyl-butan-2-ol.
482. 1-(1-imidazolyl)-3-p-isopentylthiophenyl-3-phenyl-propan-3-ol.

483. 1-(1-imidazolyl)-3-p-isopentylthiophenyl-2-methyl-3-phenyl-propan-3-ol.
484. 1-(1-imidazolyl)-3-p-isopentylthiophenyl-2-methyl-3-phenyl-propan-2-ol.
485. 1-(1-imidazolyl)-3-p-cyclohexylthiophenyl-butan-3-ol.
486. 1-(1-imidazolyl)-3-p-cyclohexylthiophenyl-2-methyl-propan-2-ol.
487. 1-(1-imidazolyl)-3-p-cyclohexylthiophenyl-2-methyl-butan-3-ol.
488. 1-(1-imidazolyl)-3-p-cyclohexylthiophenyl-2-methyl-butan-2-ol.
489. 1-(1-imidazolyl)-3-p-cyclohexylthiophenyl-3-phenyl-propan-2-ol.
490. 1-(1-imidazolyl)-3-p-cyclohexylthiophenyl-2-methyl-3-phenyl-propan-3-ol.
491. 1-(1-imidazolyl)-3-p-cyclohexylthiophenyl-2-methyl-3-phenyl-propane-2-ol.
492. 1-(1-imidazolyl)-3-(2-dibenzothienyl)-butan-3-ol.
493. 1-(1-imidazolyl)-3-(2-dibenzothienyl)-2-methyl-propan-2-ol.
494. 1-(1-imidazolyl)-3-(2-dibenzothienyl)-2-methyl-butan-3-ol.
495. 1-(1-imidazolyl)-3-(2-dibenzothienyl)-2-methyl-butan-2-ol.
496. 1-(1-imidazolyl)-3-(2-dibenzothienyl)-3-phenyl-propan-3-ol; m.p. 88°–91°.
497. 1-(1-imidazolyl)-3-(2-dibenzothienyl)-2-methyl-3-phenyl-propan-3-ol.
498. 1-(1-imidazolyl)-3-(2-dibenzothienyl)-2-methyl-3-phenyl-propan-2-ol.

EXAMPLES 499 to 501

Analogously to Example 320, by reaction of the corresponding ketones with butyl lithium and subsequent hydrolysis, there are obtained:
499. 1-(1-imidazolyl)-3-p-phenylthiophenyl-heptan-3-ol.
500. 1-(1-imidazolyl)-2-p-phenylthiobenzyl-hexan-2-ol.
501. 1-(1-imidazolyl)-2-p-isopentylthiobenzyl-hexan-2-ol.

EXAMPLE 502

A Grignard solution made from 23.3 g of 2-bromo-dibenzothiophene and 2.43 g of magnesium in 1000 ml of ether is mixed dropwise with 20 g of 1-(1-imidazolyl)-3-phenyl-propan-3-one (obtainable from 1-chloro-3-phenyl-propan-3-one and imidazole) in 400 ml of ether, with stirring at 20°. This is further stirred for two hours; the alcoholate obtained is decomposed with dilute sulphuric acid and worked up as usual to obtain 1-(1-imidazolyl)-3-(2-dibenzothienyl)-3-phenyl-propan-3-ol, m.p. 88°–91°.

EXAMPLE 503

A solution of 27.3 g of 1-chloro-3-p-isopentylthiophenyl-propan-3-ol (obtainable by Friedel-Crafts reaction of isopentylthiobenzene with 3-chloropropionyl chloride to give β-chloro-p-isopentylthiopropiophenone and Meerwein-Ponndorf reduction) in 150 ml of absolute ethanol at 0° is added to a solution of 10 g of NH₃ in 150 ml of absolute ethanol. This is further stirred for 2 hours at 20°, the solution is concentrated and worked up with aqueous sodium hydroxide solution and ether to obtain 3-p-isopentylthiophenyl-3-hydroxy-propylamine.

EXAMPLE 504

A solution of 2.17 g of 1-chloro-3-p-methylthiophenylpropan-3-ol and 30 g of methylamine in 100 ml of methanol is heated in an autoclave for 2 hours at 120°. After cooling and the usual working up, 1-methylamino-3-p-methyl-thiophenylpropan-3-ol is obtained.

EXAMPLE 505

2.73 g of 1-chloro-3-p-isopentylthiophenyl-propan-3-ol is boiled with 30 ml of morpholine for 1.5 hours, cooled, and worked up as usual to obtain 1-morpholino-3-p-isopentylthiophenyl-propan-3-ol.

EXAMPLE 506

Analogously to Example 505, from 1-chloro-3-p-methylthiophenyl-propan-3-ol and 4-methylpiperidine, 1-(4-methylpiperidino)-3-p-methylthiophenyl-propan-3-ol is obtained, hydrochloride, m.p. 121°–123°.

EXAMPLE 507

2.73 g of 1-chloro-3-p-isopentylthiophenyl-propan-3-ol is heated with 30 ml of diethylamine in an autoclave for 15 hours at 150°, cooled and worked us as usual to obtain 1-diethylamino-3-p-isopentylthiophenyl-propan-3-ol.

EXAMPLE 508

A mixture of 2.73 g of 1-chloro-3-p-isopentylthiophenylpropan-3-ol and 1.36 g of imidazole is heated for 3 hours at 140°. After cooling and the usual working up, 1-(1-imidazolyl)-3-p-isopentylthiophenyl-propan-3-ol is obtained, m.p. 89°–90°.

EXAMPLE 509

2.38 g of 3-p-isopentylthiophenyl-propan-1-ol is dissolved in 10 ml of isopropylamine and, after the addition of 0.5 g of Raney nickel is shaken for 15 hours at 160° in a tube. After cooling, filtering-off of the catalyst and evaporating, 1-isopropylamino-3-p-isopentylthiophenyl-propane is obtained.

EXAMPLE 510

25.3 g of 3-p-isopentylthiophenyl-3-hydroxy-propylamine is boiled with 1 g of p-toluene-sulphonic acid in 500 ml of toluene for 2 hours with a water separator, cooled and worked up with aqueous sodium hydroxide solution to obtain 3-p-isopentylthiophenyl-3-propen-1-amine, hydrochloride, m.p. 193°–195°.

EXAMPLE 511

A mixture of 3.23 g of 1-morpholino-3-p-isopentylthiophenyl-propan-3-ol, 0.1 g of benzene-sulphonic acid and 80 ml of benzene is boiled for 24 hours with a water separator. After the usual working up, 1-morpholino-3-p-isopentylthiophenyl-2-propene is obtained, hydrochloride, m.p. 217°–218°.

EXAMPLE 512

30.7 g of 1-dimethylamino-3-p-cyclohexyl-thiophenylbutan-3-ol is dissolved in 240 ml of ethanol and mixed with 30 ml of 37% aqueous hydrochloric acid. The mixture is boiled for 1 hour and evaporated. After the usual working up, 1-dimethylamino-3-p-cyclohexylthiophenyl-2-butene is obtained, hydrochloride, m.p. 197°–199°.

EXAMPLE 513

32.5 g of 1-(1-imidazolyl)-3-p-(p-amino-phenylthio)-phenyl-propan-3-ol is heated with 325 ml of 20% aqueous hydrochloric acid for 45 minutes at 100°. This is evaporated and worked up as usual to obtain 1-(1-imidazolyl)-3-p-(p-aminophenylthio)-phenyl-2-propene, m.p. 148°–150°.

EXAMPLES 514 to 722

From the corresponding tertiary alcohols analogously to Example 512, from the corresponding secondary alcohols analogously to Example 513, the following alkenes are obtained (whereby, for better dissolution, some dioxane can also be added):

514. 1-methylamino-3-p-phenylthiophenyl-2-propane.
515. 1-methylamino-3-p-phenylthiophenyl-2-butene.
516. 1-methylamino-3-p-phenylthiophenyl-2-methyl-2-propene.
517. 1-methylamino-3-p-phenylthiophenyl-2-methyl-2-butene.
518. 1-methylamino-3-p-phenylthiophenyl-3-phenyl-2-propene.
519. 1-methylamino-3-p-phenylthiophenyl-2-methyl-3-phenyl-2-propene.
520. 1-methylamino-3-p-(2,4-dichlorobenzylthio)-phenyl-2-propene.
521. 1-methylamino-3-p-(2,4-dichlorobenzylthio)-phenyl-2-butene.
522. 1-methylamino-3-p-(2,4-dichlorobenzylthio)-phenyl-2-methyl-2-propene.
523. 1-methylamino-3-p-(2,4-dichlorobenzylthio)-phenyl-2-methyl-2-butene.
524. 1-methylamino-3-p-(2,4-dichlorobenzylthio)-phenyl-3-phenyl-2-propene.
525. 1-methylamino-3-p-(2,4-dichlorobenzylthio)-phenyl-2-methyl-3-phenyl-2-propene.
526. 1-methylamino-3-p-isopentylthiophenyl-2-propene.
527. 1-methylamino-3-p-isopentylthiophenyl-2-butene.
528. 1-methylamino-3-p-isopentylthiophenyl-2-methyl-2-propene.
529. 1-methylamino-3-p-isopentylthiophenyl-2-methyl-2-butene.
530. 1-methylamino-3-p-isopentylthiophenyl-3-phenyl-2-propene.
531. 1-methylamino-3-p-isopentylthiophenyl-2-methyl-3-phenyl-2-propene.
532. 1-methylamino-3-p-cyclohexylthiophenyl-2-propene.
533. 1-methylamino-3-p-cyclohexylthiophenyl-2-butene.
534. 1-methylamino-3-p-cyclohexylthiophenyl-2-methyl-2-propene.
535. 1-methylamino-3-p-cyclohexylthiophenyl-2-methyl-2-butene.
536. 1-methylamino-3-p-cyclohexylthiophenyl-3-phenyl-2-propene.
537. 1-methylamino-3-p-cyclohexylthiophenyl-2-methyl-3-phenyl-2-propene.
538. 1-methylamino-3-(2-dibenzothienyl)-2-propene.
539. 1-methylamino-3-(2-dibenzothienyl)-2-butene.
540. 1-methylamino-3-(2-dibenzothienyl)-2-methyl-2-propene.
541. 1-methylamino-3-(2-dibenzothienyl)-2-methyl-2-butene.
542. 1-methylamino-3-(2-dibenzothienyl)-3-phenyl-2-propene.
543. 1-methylamino-3-(2-dibenzothienyl)-2-methyl-3-phenyl-2-propene.
544. 1-ethylamino-3-p-phenylthiophenyl-2-propene.
545. 1-ethylamino-3-p-phenylthiophenyl-2-butene.
546. 1-ethylamino-3-p-phenylthiophenyl-2-methyl-2-propene.
547. 1-ethylamino-3-p-phenylthiophenyl-2-methyl-2-butene.
548. 1-ethylamino-3-p-phenylthiophenyl-3-phenyl-2-propene.
549. 1-ethylamino-3-p-phenylthiophenyl-2-methyl-3-phenyl-2-propene.
550. 1-ethylamino-3-p-(2,4-dichlorobenzylthio)-phenyl-2-propene.
551. 1-ethylamino-3-p-(2,4-dichlorobenzylthio)-phenyl-2-butene.
552. 1-ethylamino-3-p-(2,4-dichlorobenzylthio)-phenyl-2-methyl-2-propene.
553. 1-ethylamino-3-p-(2,4-dichlorobenzylthio)-phenyl-2-methyl-2-butene.
554. 1-ethylamino-3-p-(2,4-dichlorobenzylthio)-phenyl-3-phenyl-2-propene.
555. 1-ethylamino-3-p-(2,4-dichlorobenzylthio)-phenyl-2-methyl-3-phenyl-2-propene.
556. 1-ethylamino-3-p-isopentylthiophenyl-2-propene.
557. 1-ethylamino-3-p-isopentylthiophenyl-2-butene.
558. 1-ethylamino-3-p-isopentylthiophenyl-2-methyl-2-propene.
559. 1-ethylamino-3-p-isopentylthiophenyl-2-methyl-2-butene.
560. 1-ethylamino-3-p-isopentylthiophenyl-3-phenyl-2-propene.
561. 1-ethylamino-3-p-isopentylthiophenyl-2-methyl-5-phenyl-2-propene.
562. 1-ethylamino-3-p-cyclohexylthiophenyl-2-propene.
563. 1-ethylamino-3-p-cyclohexylthiophenyl-2-butene.
564. 1-ethylamino-3-p-cyclohexylthiophenyl-2-methyl-2-propene.
565. 1-ethylamino-3-p-cyclohexylthiophenyl-2-methyl-2-butene.
566. 1-ethylamino-3-p-cyclohexylthiophenyl-3-phenyl-2-propene.
567. 1-ethylamino-3-p-cyclohexylthiophenyl-2-methyl-3-phenyl-2-propene.
568. 1-ethylamino-3-(2-dibenzothienyl)-2-propene.
569. 1-ethylamino-3-(2-dibenzothienyl)-2-butene.
570. 1-ethylamino-3-(2-dibenzothienyl)-2-methyl-2-propene.
571. 1-ethylamino-3-(2-dibenzothienyl)-2-methyl-2-butene.
572. 1-ethylamino-3-(2-dibenzothienyl)-3-phenyl-2-propene.
573. 1-ethylamino-3-(2-dibenzothienyl)-2-methyl-3-phenyl-2-propene.
574. 1-dimethylamino-3-p-phenylthiophenyl-2-propene, hydrochloride, m.p. 223°–225°.
575. 1-dimethylamino-3-p-phenylthiophenyl-2-butene, hydrochloride, m.p. 199°–201°
576. 1-dimethylamino-3-p-phenylthiophenyl-2-methyl-2propene, hydrochloride, m.p. 170°–173°.
577. 1-dimethylamino-3-p-phenylthiophenyl-2-methyl-2-butene, hydrochloride, m.p. 208°–209°.
578. 1-dimethylamino-3-p-phenylthiophenyl-3-phenyl-2-propene.
579. 1-dimethylamino-3-p-phenylthiophenyl-2-methyl-3-phenyl-2-propene.
580. 1-dimethylamino-4-p-phenylthiophenyl-3-butene.

581. 1-dimethylamino-4-p-phenylthiophenyl-3-pentene, hydrochloride, m.p. 140°-142°.
582. 1-dimethylamino-4-p-phenylthiophenyl-4-pentene.
583. 1-dimethylamino-4-p-phenylthiophenyl-4-hexene.
584. 1-dimethylamino-3-p-(p-fluorophenylthio)-phenyl-2-propene.
585. 1-dimethylamino-3-p-(o-chlorophenylthio)-phenyl-2-propene.
586. 1-dimethylamino-3-p-(m-chlorophenylthio)-phenyl-2-propene.
587. 1-dimethylamino-3-p-(p-chlorophenylthio)-phenyl-2-propene.
588. 1-dimethylamino-3-p-(2,4-dichlorophenylthio)-phenyl-2-propene.
589. 1-dimethylamino-3-p-(p-bromophenylthio)-phenyl-2-propene.
590. 1-dimethylamino-3-p-(p-iodophenylthio)-phenyl-2-propene.
591. 1-dimethylamino-3-p-(p-nitrophenylthio)-phenyl-2-propene.
592. 1-dimethylamino-3-p-(p-aminophenylthio)-phenyl-2-propene.
593. 1-dimethylamino-3-p-(p-methoxyphenylthio)-phenyl-2-propene.
594. 1-dimethylamino-3-p-(p-n-butoxyphenylthio)-phenyl-2-propene.
595. 1-dimethylamino-3-p-benzylthio-phenyl-2-propene.
596. 1-dimethylamino-3-p-(p-chlorobenzylthio)-phenyl-2-propene.
597. 1-dimethylamino-3-p-(2,4-dichlorobenzylthio)-phenyl-2-propene, hydrochloride, m.p. 153°-155°.
598. 1-dimethylamino-3-p-(2,4-dichlorobenzylthio)-phenyl-2-butene.
599. 1-dimethylamino-3-p-(2,4-dichlorobenzylthio)-phenyl-2-methyl-2-propene.
600. 1-dimethylamino-3-p-(2,4-dichlorobenzylthio)-phenyl-2-methyl-2-butene.
601. 1-dimethylamino-3-p-(2,4-dichlorobenzylthio)-phenyl-3-phenyl-2-propene.
602. 1-dimethylamino-3-p-(2,4-dichlorobenzylthio)-phenyl-2-methyl-3-phenyl-2-propene.
603. 1-dimethylamino-3-p-methylthiophenyl-2-propene.
604. 1-dimethylamino-3-p-ethylthiophenyl-2-propene.
605. 1-dimethylamino-3-p-isopropylthiophenyl-2-propene.
606. 1-dimethylamino-3-p-isobutylthiophenyl-2-propene.
607. 1-dimethylamino-3-p-isopentylthiophenyl-2-propene, hydrochloride, m.p. 203°-205°.
608. 1-dimethylamino-3-p-isopentylthiophenyl-2-butene, hydrochloride, m.p. 201°-203°.
609. 1-dimethylamino-3-p-isopentylthiophenyl-2-methyl-2-propene.
610. 1-dimethylamino-3-p-isopentylthiophenyl-2-methyl-2-butene, hydrochloride, m.p. 120°-122°.
611. 1-dimethylamino-3-p-isopentylthiophenyl-3-phenyl-2-propene.
612. 1-dimethylamino-3-p-isopentylthiophenyl-2-methyl-3-phenyl-2-propene, hydrochloride, m.p. 120°-123°.
613. 1-dimethylamino-3-p-isopentylthiophenyl-2-n-butyl-2-propene, oil.
614. 1-dimethylamino-3-p-isohexylthiophenyl-2-propene.
615. 1-dimethylamino-3-p-cyclopropylthiophenyl-2-propene.
616. 1-dimethylamino-3-p-cyclopentylthiophenyl-2-propene.
617. 1-dimethylamino-3-p-cyclohexylthiophenyl-2-propene, hydrochloride, m.p. 209°-210°, methanesulphonate, m.p. 73°-80°.
618. 1-dimethylamino-3-p-cyclohexylthiophenyl-2-butene, hydrochloride, m.p. 197°-197°.
619. 1-dimethylamino-3-p-cyclohexylthiophenyl-2-methyl-2-propene.
620. 1-dimethylamino-3-p-cyclohexylthiophenyl-2-methyl-2-butene.
621. 1-dimethylamino-3-p-cyclohexylthiophenyl-3-phenyl-2-propene.
622. 1-dimethylamino-3-p-cyclohexylthiophenyl-2-methyl-3-phenyl-2-propene, hydrochloride, m.p. 202°-204°.
623. 1-dimethylamino-3-p-cycloheptylthiophenyl-2-propene.
624. 1-dimethylamino-3-(2-dibenzothienyl)-2-propene hydrochloride, m.p. 214°-215°.
625. 1-dimethylamino-3-(2-dibenzothienyl)-2-butene, hydrochloride, m.p. 233°-234°.
626. 1-dimethylamino-3-(2-dibenzothienyl)-2-methyl-2-propene.
627. 1-dimethylamino-3-(2-dibenzothienyl)-2-methyl-2-butene.
628. 1-dimethylamino-3-(2-dibenzothienyl)-3-phenyl-2-propene, hydrochloride, m.p. 211°.
629. 1-dimethylamino-3-(2-dibenzothienyl)-2-methyl-3-phenyl-2-propene.
630. 1-diethylamino-3-p-phenylthiophenyl-2-propene.
631. 1-diethylamino-3-p-phenylthiophenyl-2-butene, hydrochloride, m.p. 144°-145°.
632. 1-diethylamino-3-p-phenylthiophenyl-2-methyl-2-propene.
633. 1-diethylamino-3-p-phenylthiophenyl-2-methyl-2-butene.
634. 1-diethylamino-3-p-phenylthiophenyl-3-phenyl-2-propene, hydrochloride, m.p. 145°-146°.
635. 1-diethylamino-3-p-phenylthiophenyl-2-methyl-3-phenyl-2-propene.
636. 1-diethylamino-3-p-(2,4-dichlorobenzylthio)-phenyl-2-propene.
637. 1-diethylamino-3-p-(2,4-dichlorobenzylthio)-phenyl-2-butene.
638. 1-diethylamino-3-p-(2,4-dichlorobenzylthio)-phenyl-2-methyl-2-propene.
639. 1-diethylamino-3-p-(2,4-dichlorobenzylthio)-phenyl-2-methyl-2-butene.
640. 1-diethylamino-3-p-(2,4-dichlorobenzylthio)-phenyl-3-phenyl-2-propene.
641. diethylamino-3-p-(2,4-dichlorobenzylthio)-phenyl-2-methyl-3-phenyl-2-propene.
642. 1-diethylamino-3-p-isopentylthiophenyl-2-propene, hydrochloride, m.p. 95°-97°.
643. 1-diethylamino-3-p-isopentylthiophenyl-2-butene.
644. 1-diethylamino-3-p-isopentylthiophenyl-2-methyl-2-propene.
645. 1-diethylamino-3-p-isopentylthiophenyl-2-methyl-2-butene.
646. 1-diethylamino-3-p-isopentylthiophenyl-3-phenyl-2-propene.
647. 1-diethylamino-3-p-isopentylthiophenyl-2-methyl-3-phenyl-2-propene.
648. 1-diethylamino-3-p-cyclohexylthiophenyl-2-propene.
649. 1-diethylamino-3-p-cyclohexylthiophenyl-2-butene.

650. 1-diethylamino-3-p-cyclohexylthiophenyl-2-methyl-2-propene, hydrochloride, m.p. 178°-180°.
651. 1-diethylamino-3-p-cyclohexylthiophenyl-2-methyl-2-butene.
652. 1-diethylamino-3-p-cyclohexylthiophenyl-3-phenyl-2-propene, hydrochloride, m.p. 123°-125°.
653. 1-diethylamino-3-p-cyclohexylthiophenyl-2-methyl-3-phenyl-2-propene.
654. 1-diethylamino-3-(2-dibenzothienyl)-2-propene.
655. 1-diethylamino-3-(2-dibenzothienyl)-2-butene.
656. 1-diethylamino-3-(2-dibenzothienyl)-2-methyl-2-propene.
657. 1-diethylamino-3-(2-dibenzothienyl)-2-methyl-2-butene.
658. 1-diethylamino-3-(2-dibenzothienyl)-3-phenyl-2-propene.
659. 1-diethylamino-3-(2-dibenzothienyl)-2-methyl-3-phenyl-2-propene.
660. 1-di-n-butylamino-3-p-isopentylthiophenyl-2-propene.
661. 1-pyrrolidino-3-p-isopentylthiophenyl-2-propene, hydrochloride, m.p. 184°-185°.
662. 1-piperidino-3-p-isopentylthiophenyl-2-propene, hydrochloride, m.p. 215°.
663. 1-(4-methylpiperidino)-3-p-methylthiophenyl-2-propene, hydrochloride, m.p. 206°-207°.
664. 1-(4-methylpiperidino)-3-p-isopentylthiophenyl-2-propene.
665. 1-morpholino-3-p-isopentylthiophenyl-2-propene, hydrochloride, m.p. 217°-218°.
666. 1-(1-imidazolyl)-3-p-phenylthiophenyl-2-propene, m.p. 59°-60°, hydrochloride, m.p. 161°-163°.
667. 1-(1-imidazolyl)-3-p-phenylthiophenyl-2-butene.
668. 1-(1-imidazolyl)-3-p-phenylthiophenyl-2-methyl-2-propene, hydrochloride, m.p. 125°-127°, hydroiodide, m.p. 131°-133°.
669. 1-(1-imidazolyl)-3-p-phenylthiophenyl-2-methyl-2-butene.
670. 1-(1-imidazolyl)-3-p-phenylthiophenyl-3-phenyl-2-propene.
671. 1-(1-imidazolyl)-3-p-phenylthiophenyl-2-methyl-3-phenyl-2-propene.
672. 1-(1-imidazolyl)-3-p-phenylthiophenyl-2-heptene.
673. 1-(1-imidazolyl)-3-p-phenylthiophenyl-2-n-butyl-2-propene.
674. 1-(1-imidazolyl)-4-p-phenylthiophenyl-3-butene.
675. 1-(1-imidazolyl)-4-p-phenylthiophenyl-3-pentene.
676. 1-(1-imidazolyl)-5-p-phenylthiophenyl-4-pentene.
677. 1-(1-imidazolyl)-5-p-phenylthiophenyl-4-hexene.
678. 1-(1-imidazolyl)-3-p-(p-fluorophenylthio)-phenyl-2-propene.
679. 1-(1-imidazolyl)-3-p-(o-chlorophenylthio)-phenyl-2-propene.
680. 1-(1-imidazolyl)-3-p-(p-chlorophenylthio)-phenyl-2-propene.
681. 1-(1-imidazolyl)-3-p-(2,4-dichlorophenylthio)-phenyl-2-propene.
682. 1-(1-imidazolyl)-3-p-(p-bromophenylthio)-phenyl-2-propene, m.p. 116°-117°.
683. 1-(1-imidazolyl)-3-p-(p-iodophenylthio)-phenyl-2-propene.
684. 1-(1-imidazolyl)-3-p-(p-nitrophenylthio)-phenyl-2-propene, m.p. 125°-128°.
685. 1-(1-imidazolyl)-3-p-(p-methoxyphenylthio)-phenyl-2-propene, hydrochloride, m.p. 158°-159°.
686. 1-(1-imidazolyl)-3-p-(p-n-butoxyphenylthio)-phenyl-2-propene.
687. 1-(1-imidazolyl)-3-p-benzylthiophenyl-2-propene.
688. 1-(1-imidazolyl)-3-p-(p-chlorobenzylthio)-phenyl-2-propene.
689. 1-(1-imidazolyl)-3-p-(2,4-dichlorobenzylthio)-phenyl-2-propene, m.p. 83°-86°.
690. 1-(1-imidazolyl)-3-p-(2,4-dichlorobenzylthio)-phenyl-2-butene.
691. 1-(1-imidazolyl)-3-p-(2,4-dichlorobenzylthio)-phenyl-2-methyl-2-propene.
692. 1-(1-imidazolyl)-3-p-(2,4-dichlorobenzylthio)-phenyl-2-methyl-2-butene.
693. 1-(1-imidazolyl)-3-p-(2,4-dichlorobenzylthio)-phenyl-3-phenyl-2-propene.
694. 1-(1-imidazolyl)-3-p-(2,4-dichlorobenzylthio)-phenyl-2-methyl-3-phenyl-2-propene.
695. 1-(1-imidazolyl)-3-p-methylthiophenyl-2-propene.
696. 1-(1-imidazolyl)-3-p-ethylthiophenyl-2-propene.
697. 1-(1-imidazolyl)-3-p-isopropylthiophenyl-2-propene.
698. 1-(1-imidazolyl)-3-p-isobutylthiophenyl-2-propene.
699. 1-(1-imidazolyl)-3-p-isopentylthiophenyl-2-propene, fumarate, m.p. 122°-124°.
700. 1-(1-imidazolyl)-3-p-isopentylthiophenyl-2-butene.
701. 1-(1-imidazolyl)-3-p-isopentylthiophenyl-2-methyl-2-propene, oil.
702. 1-(1-imidazolyl)-3-p-isopentylthiophenyl-2-methyl-2-butene.
703. 1-(1-imidazolyl)-3-p-isopentylthiophenyl-2-phenyl-2-propene.
704. 1-(1-imidazolyl)-3-p-isopentylthiophenyl-2-methyl-3-phenyl-2-propene, hydrochloride, m.p. 92°-95°.
705. 1-(1-imidazolyl)-3-p-isopentylthiophenyl-2-butyl-2-propene.
706. 1-(1-imidazolyl)-3-p-isohexylthiophenyl-2-propene.
707. 1-(1-imidazolyl)-3-p-cyclopropylthiophenyl-2-propene.
708. 1-(1-imidazolyl)-3-p-cyclopentylthiophenyl-2-propene.
709. 1-(1-imidazolyl)-3-p-cyclohexylthiophenyl-2-propene.
710. 1-(1-imidazolyl)-3-p-cyclohexylthiophenyl-2-butene, hydrochloride, m.p. 109°-111°.
711. 1-(1-imidazolyl)-3-p-cyclohexylthiophenyl-2-methyl-2-propene.
712. 1-(1-imidazolyl)-3-p-cyclohexylthiophenyl-2-methyl-2-butene.
713. 1-(1-imidazolyl)-3-p-cyclohexylthiophenyl-3-phenyl-2-propene.
714. 1-(1-imidazolyl)-3-p-cyclohexylthiophenyl-2-methyl-3-phenyl-2-propane.
715. 1-(1-imidazolyl)-3-p-cycloheptylthiophenyl-2-propane.
716. 1-(1-imidazolyl)-3-(2-dibenzothienyl)-2-propene, hydrochloride, m.p. 257°-259°.
717. 1-(1-imidazolyl)-3-(2-dibenzothienyl)-2-butene.
718. 1-(1-imidazolyl)-3-(2-dibenzothienyl)-2-methyl-2-propene.
719. 1-(1-imidazolyl)-3-(2-dibenzothienyl)-2-methyl-2-butene.
720. 1-(1-imidazolyl)-3-(2-dibenzothienyl)-3-phenyl-2-propene, hydrochloride, m.p. 214°-215°.
721. 1-(1-imidazolyl)-3-(2-dibenzothienyl)-2-methyl-3-phenyl-2-propene.
722. 1-(1,2,4-triazol-1-yl)-3-p-isopentylthiophenyl-2-propene, hydrochloride, m.p. 177°-178°.

EXAMPLE 723

A mixture of 1 g of 3-p-isopentylthiophenyl-3-hydroxy-propylamine, 2.5 ml of a 67% solution of HI in acetic acid and 5 ml of acetic acid is boiled for 90 minutes, evaporated and worked up with water and chloroform. There is obtained 3-p-isopentylthiophenyl-propylamine hydroiodide which is converted into the free base with aqueous sodium hyroxide solution.

EXAMPLE 724

A mixture of 2.85 g of 1-dimethylamino-3-(2-dibenzothienyl)-propan-3-ol, 10 ml of 67% aqueous hydriodic acid and 18 ml of acetic acid is heated for 1.5 hours at 150°. After cooling and the usual working up, 1-dimethyl-amino-3-(2-dibenzothienyl)-propane is obtained; hydrochloride, m.p. 165°–166°.

EXAMPLES 725 to 905

Analogously to Example 724, by reduction of the corresponding hydroxyamines, there is obtained:

725. 1-methylamino-3-p-phenylthiophenyl-propane.
726. 1-methylamino-3-p-phenylthiophenyl-butane.
727. 1-methylamino-3-p-phenylthiophenyl-2-methyl-propane.
728. 1-methylamino-3-p-phenylthiophenyl-2-methyl-butane.
729. 1-methylamino-3-p-phenylthiophenyl-3-phenyl-propane.
730. 1-methylamino-3-p-phenylthiophenyl-2-methyl-3-phenyl-propane.
731. 1-methylamino-3-p-(2,4-dichlorobenzylthio)-phenyl-propane.
732. 1-methylamino-3-p-(2,4-dichlorobenzylthio)-phenyl-butane.
733. 1-methylamino-3-p-(2,4-dichlorobenzylthio)-phenyl-2-methyl-propane.
734. 1-methylamino-3-p-(2,4-dichlorobenzylthio)-phenyl-2-methyl-butane.
735. 1-methylamino-3-p-(2,4-dichlorobenzylthio)-phenyl-3-phenyl-propane.
736. 1-methylamino-3-p-(2,4-dichlorobenzylthio)-phenyl-2-methyl-3-phenyl-propane.
737. 1-methylamino-3-p-isopentylthiophenyl-propane.
738. 1-methylamino-3-p-isopentylthiophenyl-butane.
739. 1-methylamino-3-p-isopentylthiophenyl-2-methyl-propane.
740. 1-methylamino-3-p-isopentylthiophenyl-2-methyl-butane.
741. 1-methylamino-3-p-isopentylthiophenyl-3-phenyl-propane.
742. 1-methylamino-3-p-isopentylthiophenyl-2-methyl-3-phenyl-propane.
743. 1-methylamino-3-p-cyclohexylthiophenyl-propane.
744. 1-methylamino-3-p-cyclohexylthiophenyl-butane.
745. 1-methylamino-3-p-cyclohexylthiophenyl-2-methyl-propane.
746. 1-methylamino-3-p-cyclohexylthiophenyl-2-methyl-butane.
747. 1-methylamino-3-p-cyclohexylthiophenyl-3-phenyl-propane.
748. 1-methylamino-3-p-cyclohexylthiophenyl-2-methyl-3-phenyl-propane.
749. 1-methylamino-3-(2-dibenzothienyl)-propane.
750. 1-methylamino-3-(2-dibenzothionyl)-butane.
751. 1-methylamino-3-(2-dibenzothienyl)-2-methyl-propane.
752. 1-methylamino-3-(2-dibenzothienyl)-2-methyl-butane.
753. 1-methylamino-3-(2-dibenzothienyl)-3-phenyl-propane.
754. 1-methylamino-3-(2-dibenzothienyl)-2-methyl-3-phenyl-propane.
755. 1-ethylamino-3-p-phenylthiophenyl-propane.
756. 1-ethylamino-3-p-phenylthiophenyl-butane.
757. 1-ethylamino-3-p-phenylthiophenyl-2-methyl-propane.
758. 1-ethylamino-3-p-phenylthiophenyl-2-methyl-butane.
759. 1-ethylamino-3-p-phenylthiophenyl-3-phenyl-propane.
760. 1-ethylamino-3-p-phenylthiophenyl-2-methyl-3-phenyl-propane.
761. 1-ethylamino-3-p-(2,4-dichlorobenzylthio)-phenyl-propane.
762. 1-ethylamino-3-p-(2,4-dichlorobenzylthio)-phenyl-butane.
763. 1-ethylamino-3-p-(2,4-dichlorobenzylthio)-phenyl-2-methyl-propane.
764. 1-ethylamino-3-p-(2,4-dichlorobenzylthio)-phenyl-2-methyl-butane.
765. 1-ethylamino-3-p-(2,4-dichlorobenzylthio)-phenyl-3-phenyl-propane.
766. 1-ethylamino-3-p-(2,4-dichlorobenzylthio)-phenyl-2-methyl-3-phenyl-propane.
767. 1-ethylamino-3-p-isopentylthiophenyl-propane.
768. 1-ethylamino-3-p-isopentylthiophenyl-butane.
769. 1-ethylamino-3-p-isopentylthiophenyl-2-methyl-propane.
770. 1-ethylamino-3-p-isopentylthiophenyl-2-methyl-butane.
771. 1-ethylamino-3-p-isopentylthiophenyl-3-phenyl-propane.
772. 1-ethylamino-3-p-isopentylthiophenyl-2-methyl-3-phenyl-propane.
773. 1-ethylamino-3-p-cyclohexylthiophenyl-propane.
774. 1-ethylamino-3-p-cyclohexylthiophenyl-butane.
775. 1-ethylamino-3-p-cyclohexylthiophenyl-2-methyl-propane.
776. 1-ethylamino-3-p-cyclohexylthiophenyl-2-methyl-butane.
777. 1-ethylamino-3-p-cyclohexylthiophenyl-3-phenyl-propane.
778. 1-ethylamino-3-p-cyclohexylthiophenyl-2-methyl-3-phenyl-propane.
779. 1-ethylamino-3-(2-dibenzothienyl)-propane.
780. 1-ethylamino-3-(2-dibenzothienyl)-butane.
781. 1-ethylamino-3-(2-dibenzothienyl)-2-methyl-propane.
782. 1-ethylamino-3-(2-dibenzothienyl)-2-methyl-butane.
783. 1-ethylamino-3-(2-dibenzothienyl)-3-phenyl-propane.
784. 1-ethylamino-3-(2-dibenzothienyl)-2-methyl-3-phenyl-propane.
785. 1-dimethylamino-3-p-phenylthiophenyl-propane.
786. 1-dimethylamino-3-p-phenylthiophenyl-butane.
787. 1-dimethylamino-3-p-phenylthiophenyl-2-methyl-propane, hydrochloride, m.p. 131°–134°.
788. 1-dimethylamino-3-p-phenylthiophenyl-2-methyl-butane.
789. 1-dimethylamino-3-p-phenylthiophenyl-3-phenyl-propane.
790. 1-dimethylamino-3-p-phenylthiophenyl-2-methyl-3-phenyl-propane.

791. 1-dimethylamino-4-p-phenylthiophenyl-butane.
792. 1-dimethylamino-4-p-phenylthiophenyl-pentane.
793. 1-dimethylamino-5-p-phenylthiophenyl-pentane.
794. 1-dimethylamino-5-p-phenylthiophenyl-hexane.
795. 1-dimethylamino-3-p-(p-fluorophenylthio)-phenyl-propane.
796. 1-dimethylamino-3-p-(o-chlorophenylthio)-phenyl-propane.
797. 1-dimethylamino-3-p-(p-chlorophenylthio)-phenyl-propane.
798. 1-dimethylamino-3-p-(2,4-dichlorophenylthio)-phenyl-propane.
799. 1-dimethylamino-3-p-(p-bromophenylthio)-phenyl-propane.
800. 1-dimethylamino-3-p-(p-iodophenylthio)-phenyl-propane.
801. 1-dimethylamino-3-p-(p-nitrophenylthio)-phenyl-propane.
802. 1-dimethylamino-3-p-(p-aminophenylthio)-phenyl-propane.
803. 1-dimethylamino-3-p-(p-methoxyphenylthio)-phenyl-propane.
804. 1-dimethylamino-3-p-(p-n-butoxyphenylthio)-phenyl-propane.
805. 1-dimethylamino-3-p-benzylthiophenyl-propane.
806. 1-dimethylamino-3-p-(p-chlorobenzylthio)-phenyl-propane.
807. 1-dimethylamino-3-p-(2,4-dichlorobenzylthio)-phenyl-propane, hydrochloride, m.p. 97°-100°.
808. 1-dimethylamino-3-p-(2,4-dichlorobenzylthio)-phenyl-butane.
809. 1-dimethylamino-3-p-(2,4-dichlorobenzylthio)-phenyl-2-methyl-propane.
810. 1-dimethylamino-3-p-(2,4-dichlorobenzylthio)-phenyl-2-methyl-butane.
811. 1-dimethylamino-3-p-(2,4-dichlorobenzylthio)-phenyl-3-phenyl-propane.
812. 1-dimethylamino-3-p-(2,4-dichlorobenzylthio)-phenyl-2-methyl-3-phenyl-propane.
813. 1-dimethylamino-3-p-methylthiophenyl-propane.
814. 1-dimethylamino-3-p-ethylthiophenyl-propane.
815. 1-dimethylamino-3-p-isopropylthiophenyl-propane.
816. 1-dimethylamino-3-p-isobutylthiophenyl-propane.
817. 1-dimethylamino-3-p-isopentylthiophenyl-propane, hydrochloride, m.p. 148°-150°.
818. 1-dimethylamino-3-p-isopentylthiophenyl-butane.
819. 1-dimethylamino-3-p-isopentylthiophenyl-2-methyl-propane, hydrochloride, m.p. 148°-150°.
820. 1-dimethylamino-3-p-isopentylthiophenyl-2-methylbutane, hydrochloride, m.p. 118°-120°.
821. 1-dimethylamino-3-p-isopentylthiophenyl-3-phenyl-propane.
822. 1-dimethylamino-3-p-isopentylthiophenyl-2-methyl-3-phenyl-propane, hydrochloride, m.p. 110°-111°.
823. 1-dimethylamino-3-p-isohexylthiophenyl-propane.
824. -dimethylamino-3-p-cyclopropylthiophenyl-propane.
825. 1-dimethylamino-3-p-cyclopentylthiophenyl-propane.
826. 1-dimethylamino-3-p-cyclohexylthiophenyl-propane.
827. 1-dimethylamino-3-p-cyclohexylthiophenyl-butane.
828. 1-dimethylamino-3-p-cyclohexylthiophenyl-2-methyl-propane.
829. 1-dimethylamino-3-p-cyclohexylthiophenyl-2-methylbutane.
830. 1-dimethylamino-3-p-cyclohexylthiophenyl-3-phenyl-propane.
831. 1-dimethylamino-3-p-cyclohexylthiophenyl-2-methyl-3-phenyl-propane.
832. 1-dimethylamino-3-p-cycloheptylthiophenylpropane.
833. 1-dimethylamino-3-(2-dibenzothienyl)-butane, hydrochloride, m.p. 175°-177°.
834. 1-dimethylamino-3-(2-dibenzothienyl)-2-methyl-propane.
835. 1-dimethylamino-3-(2-dibenzothienyl)-2-methyl-butane.
836. 1-dimethylamino-3-(2-dibenzothienyl)-3-phenyl-propane, hydrochloride, m.p. 193°-195°.
837. 1-dimethylamino-3-(2-dibenzothienyl)-2-methyl-3-phenyl-propane.
838. 1-diethylamino-3-p-phenylthiophenyl-propane.
839. 1-diethylamino-3-p-phenylthiophenyl-butane.
840. 1-diethylamino-3-p-phenylthiophenyl-2-methyl-propane.
841. 1-diethylamino-3-p-phenylthiophenyl-2-methyl-butane.
842. 1-diethylamino-3-p-phenylthiophenyl-3-phenyl-propane.
843. 1-diethylamino-3-p-phenylthiophenyl-2-methyl-3-phenyl-propane.
844. 1-diethylamino-3-p-(2,4-dichlorobenzylthio)-phenyl-propane.
845. 1-diethylamino-3-p-(2,4-dichlorobenzylthio)-phenyl-butane.
846. 1-diethylamino-3-p-(2,4-dichlorobenzylthio)-phenyl-2-methyl-propane.
847. 1-diethylamino-3-p-(2,4-dichlorobenzylthio)-phenyl-2-methyl-butane.
848. 1-diethylamino-3-p-(2,4-dichlorobenzylthio)-phenyl-3-phenyl-propane.
849. 1-diethylamino-3-p-(2,4-dichlorobenzylthio)-phenyl-2-methyl-3-phenyl-propane.
850. 1-diethylamino-3-p-isopentylthiophenyl-propane.
851. 1-diethylamino-3-p-isopentylthiophenyl-butane.
852. 1-diethylamino-3-p-isopentylthiophenyl-2-methyl-propane.
853. 1-diethylamino-3-p-isopentylthiophenyl-2-methyl-butane.
854. 1-diethylamino-3-p-isopentylthiophenyl-3-phenyl-propane.
855. 1-diethylamino-3-p-isopentylthiophenyl-2-methyl-3-phenyl-propane.
856. 1-diethylamino-3-p-cyclohexylthiophenyl-propane.
857. 1-diethylamino-3-p-cyclohexylthiophenyl-butane.
858. 1-diethylamino-3-p-cyclohexylthiophenyl-2-methyl-propane.
859. 1-diethylamino-3-p-cyclohexylthiophenyl-2-methyl-butane.
860. 1-diethylamino-3-p-cyclohexylthiophenyl-3-phenyl-propane.
861. 1-diethylamino-3-p-cyclohexylthiophenyl-2-methyl-3-phenyl-propane.
862. 1-diethylamino-3-(2-dibenzothienyl)-propane, hydrochloride, m.p. 118°-121°.
863. 1-diethylamino-3-(2-dibenzothienyl)-butane.
864. 1-diethylamino-3-(2-dibenzothienyl)-2-methyl-propane.
865. 1-diethylamino-3-(2-dibenzothienyl)-2-methyl-butane.
866. 1-diethylamino-3-(2-dibenzothienyl)-3-phenyl-propane.

867. 1-diethylamino-3-(2-dibenzothienyl)-2-methyl-3-phenyl-propane.
868. 1-di-n-butylamino-3-p-isopentylthiophenyl-propane.
869. 1-pyrrolidino-3-p-isopentylthiophenyl-propane.
870. 1-piperidino-3-p-isopentylthiophenyl-propane.
871. 1-(4-methylpiperidino)-3-p-isopentylthiophenyl-propane.
872. 1-morpholino-3-p-isopentylthiophenyl-propane.
873. 1-(1-imidazolyl)-3-p-phenylthiophenyl-2-methyl-propane, hydrochloride, m.p. 120°–122°.
874. 1-(1-imidazolyl)-3-p-phenylthiophenyl-2-methyl-butane.
875. 1-(1-imidazolyl)-3-p-phenylthiophenyl-2-methyl-3-phenyl-propane.
876. 1-(1-imidazolyl)-3-p-phenylthiophenyl-2-n-butyl-propane.
877. 1-(1-imidazolyl)-3-p-(2,4-dichlorobenzylthio)-phenyl-2-methyl-propane.
878. 1-(1-imidazolyl)-3-p-(2,4-dichlorobenzylthio)-phenyl-2-methyl-butane.
879. 1-(1-imidazolyl)-3-p-(2,4-dichlorobenzylthio)-phenyl-2-methyl-3-phenyl-propane.
880. 1-(1-imidazolyl)-3-p-methylthiophenyl-propane.
881. 1-(1-imidazolyl)-3-p-ethylthiophenyl-propane.
882. 1-(1-imidazolyl)-3-p-isopropylthiophenyl-propane.
883. 1-(1-imidazolyl)-3-p-isobutylthiophenyl-propane.
884. 1-(1-imidazolyl)-3-p-isopentylthiophenyl-propane, oil.
885. 1-(1-imidazolyl)-3-p-isopentylthiophenyl-butane.
886. 1-(1-imidazolyl)-3-p-isopentylthiophenyl-2-methyl-propane, hydrochloride, m.p. 97°–99°.
887. 1-(1-imidazolyl)-3-p-isopentylthiophenyl-2-methyl-butane, oil.
888. 1-(1-imidazolyl)-3-p-isopentylthiophenyl-3-phenyl-propane, hydrochloride, m.p. 85°–87°.
889. 1-(1-imidazolyl)-3-p-isopentylthiophenyl-2-methyl-3-phenyl-propane, hydrochloride, m.p. 158°–160°.
890. 1-(1-imidazolyl)-3-p-isohexylthiophenyl-propane.
891. 1-(1-imidazolyl)-3-p-cyclopropylthiophenyl-propane.
892. 1-(1-imidazolyl)-3-p-cyclopentylthiophenyl-propane.
893. 1-(1-imidazolyl)-3-p-cyclohexylthiophenyl-propane.
894. 1-(1-imidazolyl)-3-p-cyclohexylthiophenyl-butane.
895. 1-(1-imidazolyl)-3-p-cyclohexylthiophenyl-2-methyl-propane.
896. 1-(1-imidazolyl)-3-p-cyclohexylthiophenyl-2-methyl-butane.
897. 1-(1-imidazolyl)-3-p-cyclohexylthiophenyl-3-phenyl-propane.
898. 1-(1-imidazolyl)-3-p-cyclohexylthiophenyl-2-methyl-3-phenyl-propane.
899. 1-(1-imidazolyl)-3-(2-dibenzothienyl)-propane, hydrochloride, m.p. 159°–160°.
900. 1-(1-imidazolyl)-3-(2-dibenzothienyl)-butane, oil.
901. 1-(1-imidazolyl)-3-(2-dibenzothienyl)-2-methyl-propane.
902. 1-(1-imidazolyl)-3-(2-dibenzothienyl)-2-methyl-butane.
903. 1-(1-imidazolyl)-3-(2-dibenzothienyl)-3-phenyl-propane, m.p. 194°–195°.
904. 1-(1-imidazolyl)-3-(2-dibenzothienyl)-2-methyl-3-phenyl-propane.
905. 1-(1,2,4-triazol-1-yl)-3-p-isopentylthiophenyl-propane.

EXAMPLE 906

A solution of 28.1 g of 1-dimethylamino-3-(2-dibenzothienyl)-2-butene in 500 ml of methanol is hydrogenated on 10 g of 5% Pd-C at 20° and normal pressure up to the end of the hydrogen take up. This is filtered and evaporated to obtain 1-dimethylamino-3-(2-dibenzothienyl)-butane, hydrochloride, m.p. 176°–177°.

EXAMPLE 907

A solution of 2.51 g of 3-p-isopentylthiophenyl-butylamine and 1.5 g of benzaldehyde in 25 ml of benzene is boiled for 2 hours on a water separator. The solution of the 1-benzylideneamino-3-p-isopentylthiophenyl-butane obtained is heated with 5 g of methyl iodide for 12 hours at 150° in a tube and thereafter evaporated. The quaternary salt obtained is boiled for 10 minutes in 90% ethanol. Again, this is evaporated, taken up in dilute hydrochloric acid and the split off benzaldehyde is extracted with ether. The acidic aqueous solution is rendered alkaline with aqueous sodium hydroxide solution and worked up as usual. 1-methylamino-3-p-isopentylthiophenyl-butane is obtained.

EXAMPLE 908

A mixture of 2.72 g of 3-p-isopentylthiophenyl-2-propen-1-amine hydrochloride, 5 ml of formic acid, 0.7 g of sodium formate and 4 ml of 40% formaldehyde solution is heated for 3 hours at 60° and thereafter for 12 hours at 100°. After the usual working up, 1-dimethylamino-3-p-isopentylthiophenyl-2-propene is obtained, hydrochloride, m.p. 203°–205°.

EXAMPLE 909

A mixture of 2.83 g of 1-isopropylamino-3-(2-dibenzothienyl)-propane, 12 ml of formic acid and 2 g of 40% formaldehyde solution is heated for 3 hours at 60°, then for 12 hours at 100° and subsequently evaporated. After the usual working up, 1-(N-methyl-N-isopropylamino)-3-(2-dibenzothienyl)-propane is obtained.

EXAMPLE 910

A mixture of 2.37 g of 3-p-isopentylthiophenyl-propylamine, 1.38 g of potassium carbonate, 2.53 g of 1,5-dibromopentane and 15 ml of n-butanol is boiled for 24 hours, while stirring. This is filtered off with suction, the filtrate evaporated and worked up as usual to obtain 1-piperidino-3-p-isopentylthiophenyl-propane.

The following Examples concern pharmaceutical compositions which contain the thioethers of formula I or their acid-addition salts:

EXAMPLE A: Tablets

A mixture of 1 kg of 1-(1-imidazolyl)-3-(2-dibenzothienyl)-propane hydrochloride, 4 kg of lactose, 1.2 kg of potato starch, 0.2 kg of talc and 0.1 kg of magnesium stearate is pressed into tablets in a conventional manner so that each tablet contains 50 mg of active material.

EXAMPLE B: Dragees

Analogously to Example A, tablets are pressed which are subsequently coated in the conventional fashion with a coating of saccharose, potato starch, talc, tragacanth and coloring material.

EXAMPLE C: Capsules 10 kg of 1-(1-imidazolyl)-3-(2-dibenzothienyl)-propane hydrochloride are filled in the conventional fashion into hard gelatine capsules so that each capsule contains 50 mg of active material.

EXAMPLE D: Ampoules

A solution of 1 kg of 1-(1-imidazolyl)-3-(2-dibenzothienyl)-propane hydrochloride in 30 l of double distilled water is sterile filtered, filled into ampoules, lyophilized under sterile conditions and sterilely closed. Each ampoule contains 20 mg of active material.

EXAMPLE E: Salve 2 kg of 1-(1-imidazolyl)-3-p-phenylthiophenyl-2-methyl-2-propene hydrochloride is dissolved in a warm liquid mixture of 40 kg of polyethylene glycol 400 and 58 kg of polyethylene glycol 1500. The solution is stirred during cooling and used as a salve for the treatment of fungal and bacterial infections.

EXAMPLE F: Cream

In conventional fashion, a mixture of 20 kg of 1-(1-imidazolyl)-3-p-phenylthiophenyl-2-methyl-2-propene hydrochloride, 200 kg of polyethylene glycol 1000 monocetyl ether, 50 kg of polyethylene glycol 1500 monocetyl ether, 150 kg of Vaseline, 50 kg of paraffin oil and 2 kg of sorbic acid is warmed, allowed to cool and stirred into 528 kg of water.

EXAMPLE G: Cream

A mixture of 2 kg of 1-(1-imidazolyl)-3-p-phenylthiophenyl-2-methyl-2-propene hydrochloride, 5 kg of 1,2-propanediol, 5 kg of glycerol stearate, 5 kg of spermaceti, 10 kg of isopropyl myristate and 4 kg of polysorbate 60 is warmed, allowed to cool and stirred into 69 kg of water.

EXAMPLE H: Solution 2 kg of 1-(1-imidazolyl)-3-p-phenylthiophenyl-2-methyl-2-propene hydrochloride are dissolved in 98 kg of 1,2-propane diol. The solution is used for the treatment of fungal and bacterial infections.

EXAMPLE I: Spray

The spray consists of a solution of 1 (part by weight) of 1-(1-imidazolyl)-3-p-phenylthiophenyl-2-propene hydrochloride, 10 of isopropyl myristate, 15 of paraffin oil, 30 of ethanol and 44 of isopropanol.

Tablets, dragees, capsules, ampoules, salves, creams, solutions and sprays are obtainable analogously which contain one or more of the other active materials of formula I and/or their physiologically acceptable salts.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A thioether of the formula

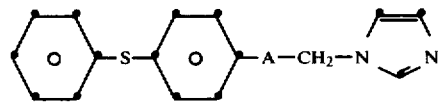

wherein A is —CH=CH—, —CH=C(CH$_3$)— or —CH$_2$—CH(CH$_3$)—.

2. 1-(1-imidazolyl)-3-p-phenylthiophenyl-2-propene, a compound of claim 1.

3. 1-(1-imidazolyl)-3-p-phenylthiophenyl-2-methyl-2-propene, a compound of claim 1.

4. 1-(1-imidazolyl)-3-p-phenylthiophenyl-2-methylpropane, a compound of claim 1.

5. A pharmaceutical composition comprising an antimicroorganismically effective amount of a thioether of claim 1 and a pharmaceutically acceptable carrier.

6. A pharmaceutical composition comprising from 5–500 mg of a thioether of claim 1 and a pharmaceutically acceptable carrier.

7. A method of treating infection due to microorganisms which comprises administering an antimicroorganismically effective amount of a thioether of claim 1.

* * * * *